(12) United States Patent
McLean et al.

(10) Patent No.: US 8,834,492 B2
(45) Date of Patent: Sep. 16, 2014

(54) CONTINUOUS INDENTATION LATERAL LOBE APPARATUS AND METHOD

(75) Inventors: Matthew McLean, San Francisco, CA (US); Floria Cheng, San Francisco, CA (US); Theodore C. Lamson, Pleasanton, CA (US); Joseph Catanese, III, San Leandro, CA (US); Ling-Kang Tong, Fremont, CA (US); Michael Gearhart, Fremont, CA (US); Kevin McDermott, Pleasanton, CA (US); Ben Thompson, San Carlos, CA (US); Earl A. Bright, II, Los Altos, CA (US)

(73) Assignee: NeoTract, Inc., Pleasanton, CA (US)

( * ) Notice: Subject to any disclaimer, the term of this patent is extended or adjusted under 35 U.S.C. 154(b) by 246 days.

(21) Appl. No.: 12/979,089

(22) Filed: Dec. 27, 2010

(65) Prior Publication Data
US 2011/0160747 A1  Jun. 30, 2011

Related U.S. Application Data

(63) Continuation-in-part of application No. 12/852,243, filed on Aug. 6, 2010, now Pat. No. 8,333,776, and a (Continued)

(51) Int. Cl.
| | |
|---|---|
| *A61B 17/10* | (2006.01) |
| *A61B 17/04* | (2006.01) |
| *A61B 17/32* | (2006.01) |
| *A61B 17/29* | (2006.01) |
| *A61B 17/00* | (2006.01) |
| *A61B 18/00* | (2006.01) |
| *A61B 17/34* | (2006.01) |
| *A61B 17/064* | (2006.01) |
| *A61B 17/42* | (2006.01) |
| *A61B 17/06* | (2006.01) |

(52) U.S. Cl.
CPC ............ *A61B 17/0401* (2013.01); *A61B 17/32* (2013.01); *A61B 2017/2925* (2013.01); *A61B 2017/00022* (2013.01); *A61B 2017/00792* (2013.01); *A61B 2017/00805* (2013.01); *A61B 2017/0046* (2013.01); *A61B 2018/00547* (2013.01); *A61B 17/3468* (2013.01); *A61B 2017/00867* (2013.01); *A61B 17/064* (2013.01); *A61B 17/3478* (2013.01); *A61B 2017/00796* (2013.01); *A61B 2017/0409* (2013.01); *A61B 2017/0417* (2013.01); *A61B 2017/0404* (2013.01); *A61B 17/42* (2013.01); *A61B 2017/0464* (2013.01); *A61B 17/0469* (2013.01); *A61B 2017/00274* (2013.01); *A61B 2017/0479* (2013.01); *A61B 2017/06052* (2013.01); *A61B 17/00234* (2013.01); *A61B 2017/0488* (2013.01); *A61B 2017/0419* (2013.01); *A61B 2017/06095* (2013.01)
USPC ............................ 606/139; 606/151; 606/232

(58) Field of Classification Search
USPC .................. 606/139, 232, 140, 144, 151, 153
See application file for complete search history.

(56) References Cited

U.S. PATENT DOCUMENTS

| | | | |
|---|---|---|---|
| 659,422 | A | 10/1900 | Shidler |
| 780,392 | A | 1/1905 | Wanamaker et al. |

(Continued)

FOREIGN PATENT DOCUMENTS

| | | |
|---|---|---|
| DE | 10159470 | 6/2003 |
| EP | 0246836 | 12/1991 |

(Continued)

OTHER PUBLICATIONS

Richard Berges et al., "Alternative Minimalinvasive Therapien Beim Benignen Prostatasyndrom", Medizin, Jg. 104, Heft 37, Sep. 14, 2007.

(Continued)

*Primary Examiner* — Gregory Anderson

(57) ABSTRACT

A system and associated method for manipulating tissues and anatomical or other structures in medical applications for the purpose of treating diseases or disorders or other purposes. In one aspect, the system includes a delivery device configured to deploy and implant anchor devices for creating continuous defects or indentations in lobes of a prostate.

23 Claims, 24 Drawing Sheets

Related U.S. Application Data continuation-in-part of application No. 12/512,674, filed on Jul. 30, 2009, now Pat. No. 8,216,254, application No. 12/979,089, which is a continuation-in-part of application No. 11/775,162, filed on Jul. 9, 2007, and a continuation-in-part of application No. 11/671,914, filed on Feb. 6, 2007, now Pat. No. 8,157,815, and a continuation-in-part of application No. 11/492,690, filed on Jul. 24, 2006, now Pat. No. 7,896,891, and a continuation-in-part of application No. 11/833,660, filed on Aug. 3, 2007, which is a continuation of application No. 11/318,246, filed on Dec. 22, 2005, now Pat. No. 7,645,286, application No. 12/979,089, which is a continuation-in-part of application No. 11/838,036, filed on Aug. 13, 2007, now Pat. No. 7,914,542, which is a continuation of application No. 11/134,870, filed on May 20, 2005, now Pat. No. 7,758,594.

(60) Provisional application No. 61/084,937, filed on Jul. 30, 2008.

(56) References Cited

U.S. PATENT DOCUMENTS

| | | |
|---|---|---|
| 789,467 A | 5/1905 | West |
| 2,579,192 A | 12/1951 | Kohl |
| 2,646,298 A | 7/1953 | Leary |
| 2,697,624 A | 12/1954 | Thomas et al. |
| 2,734,299 A | 2/1956 | Masson |
| 2,825,592 A | 3/1958 | Semple |
| 3,326,586 A | 6/1967 | Frost et al. |
| 3,470,834 A | 10/1969 | Bone |
| 3,521,918 A | 7/1970 | Hammond |
| 3,664,345 A | 5/1972 | Dabbs et al. |
| 3,713,680 A | 1/1973 | Pagano |
| 3,716,058 A | 2/1973 | Tanner, Jr. |
| 3,756,638 A | 9/1973 | Stockberger |
| 3,873,140 A | 3/1975 | Bloch |
| 3,875,648 A | 4/1975 | Bone |
| 3,931,667 A | 1/1976 | Merser et al. |
| 3,976,079 A | 8/1976 | Samuels et al. |
| 4,006,747 A | 2/1977 | Kronenthal et al. |
| 4,210,148 A | 7/1980 | Stivala |
| 4,235,238 A | 11/1980 | Ogiu et al. |
| 4,291,698 A | 9/1981 | Fuchs et al. |
| 4,409,974 A | 10/1983 | Freedland |
| 4,493,323 A | 1/1985 | Albright et al. |
| 4,513,746 A | 4/1985 | Aranyi |
| 4,621,640 A | 11/1986 | Mulhollan et al. |
| 4,657,461 A | 4/1987 | Smith |
| 4,669,473 A | 6/1987 | Richards et al. |
| 4,705,040 A | 11/1987 | Mueller et al. |
| 4,714,281 A | 12/1987 | Peck |
| 4,738,255 A | 4/1988 | Goble et al. |
| 4,741,330 A | 5/1988 | Hayhurst |
| 4,744,364 A | 5/1988 | Kensey |
| 4,750,492 A | 6/1988 | Jacobs |
| 4,762,128 A | 8/1988 | Rosenbluth |
| 4,823,794 A | 4/1989 | Pierce |
| 4,899,743 A | 2/1990 | Nicholson et al. |
| 4,926,860 A | 5/1990 | Stice et al. |
| 4,946,468 A | 8/1990 | Li |
| 4,955,913 A | 9/1990 | Robinson |
| 4,968,315 A | 11/1990 | Gatturna et al. |
| 5,002,550 A | 3/1991 | Li |
| 5,041,129 A | 8/1991 | Hayhurst et al. |
| 5,046,513 A | 9/1991 | Gatturna et al. |
| 5,053,046 A | 10/1991 | Janese |
| 5,080,660 A | 1/1992 | Buelna |
| 5,100,421 A | 3/1992 | Christoudias |
| 5,123,914 A | 6/1992 | Cope |
| 5,129,912 A | 7/1992 | Noda et al. |
| 5,192,303 A | 3/1993 | Gatturna et al. |
| 5,203,787 A | 4/1993 | Noblitt et al. |
| 5,207,672 A | 5/1993 | Roth et al. |
| 5,217,470 A | 6/1993 | Weston |
| 5,217,486 A | 6/1993 | Rice et al. |
| 5,234,454 A | 8/1993 | Bangs |
| 5,236,445 A | 8/1993 | Hayhurst et al. |
| 5,258,015 A | 11/1993 | Li et al. |
| 5,267,960 A | 12/1993 | Hayman et al. |
| 5,269,809 A | 12/1993 | Hayhurst et al. |
| 5,322,501 A | 6/1994 | Mahmud-Durrani |
| 5,330,488 A | 7/1994 | Goldrath |
| 5,334,200 A | 8/1994 | Johnson |
| 5,336,240 A | 8/1994 | Metzler et al. |
| 5,354,271 A | 10/1994 | Voda |
| 5,358,511 A | 10/1994 | Gatturna et al. |
| 5,364,408 A | 11/1994 | Gordon |
| 5,366,490 A * | 11/1994 | Edwards et al. ............... 607/99 |
| 5,368,599 A | 11/1994 | Hirsch et al. |
| 5,370,646 A | 12/1994 | Reese et al. |
| 5,380,334 A | 1/1995 | Torrie et al. |
| 5,391,182 A | 2/1995 | Chin |
| 5,403,348 A | 4/1995 | Bonutti |
| 5,405,352 A | 4/1995 | Weston |
| 5,411,520 A | 5/1995 | Nash et al. |
| 5,417,691 A | 5/1995 | Hayhurst |
| 5,435,805 A | 7/1995 | Edwards et al. |
| 5,470,337 A | 11/1995 | Moss |
| 5,472,446 A | 12/1995 | de la Torre |
| 5,480,406 A | 1/1996 | Nolan et al. |
| 5,499,994 A | 3/1996 | Tihon et al. |
| 5,501,690 A | 3/1996 | Measamer et al. |
| 5,507,754 A | 4/1996 | Green et al. |
| 5,522,846 A | 6/1996 | Bonutti |
| 5,531,763 A | 7/1996 | Mastri et al. |
| 5,536,240 A | 7/1996 | Edwards et al. |
| 5,540,704 A | 7/1996 | Gordon et al. |
| 5,545,171 A | 8/1996 | Sharkey et al. |
| 5,545,178 A | 8/1996 | Kensey et al. |
| 5,550,172 A | 8/1996 | Regula et al. |
| 5,554,162 A | 9/1996 | DeLange |
| 5,554,171 A | 9/1996 | Gatturna et al. |
| 5,562,689 A | 10/1996 | Green et al. |
| 5,569,305 A | 10/1996 | Bonutti |
| 5,571,104 A | 11/1996 | Li |
| 5,573,540 A | 11/1996 | Yoon |
| 5,578,044 A | 11/1996 | Gordon et al. |
| 5,591,177 A | 1/1997 | Lehrer |
| 5,593,421 A | 1/1997 | Bauer |
| 5,611,515 A | 3/1997 | Benderev et al. |
| 5,626,614 A | 5/1997 | Hart |
| 5,630,824 A | 5/1997 | Hart |
| 5,647,836 A | 7/1997 | Blake, III et al. |
| 5,665,109 A | 9/1997 | Yoon |
| 5,667,486 A | 9/1997 | Mikulich et al. |
| 5,669,917 A | 9/1997 | Sauer et al. |
| 5,690,677 A | 11/1997 | Schmieding et al. |
| 5,697,950 A | 12/1997 | Fucci et al. |
| 5,707,394 A | 1/1998 | Miller et al. |
| 5,716,368 A | 2/1998 | de la Torre et al. |
| 5,718,717 A | 2/1998 | Bonutti |
| 5,725,556 A | 3/1998 | Moser et al. |
| 5,725,557 A | 3/1998 | Gatturna et al. |
| 5,733,306 A | 3/1998 | Bonutti |
| 5,741,276 A | 4/1998 | Poloyko et al. |
| 5,746,753 A | 5/1998 | Sullivan et al. |
| 5,749,846 A | 5/1998 | Edwards et al. |
| 5,752,963 A | 5/1998 | Allard et al. |
| 5,782,862 A | 7/1998 | Bonutti |
| 5,782,864 A | 7/1998 | Lizardi |
| 5,800,445 A | 9/1998 | Ratcliff et al. |
| 5,807,403 A | 9/1998 | Beyar et al. |
| 5,810,848 A | 9/1998 | Hayhurst |
| 5,814,072 A | 9/1998 | Bonutti |
| 5,830,179 A | 11/1998 | Mikus et al. |
| 5,830,221 A | 11/1998 | Stein |
| 5,845,645 A | 12/1998 | Bonutti |
| 5,846,254 A | 12/1998 | Schulze et al. |
| 5,861,002 A | 1/1999 | Desai |

(56) References Cited

U.S. PATENT DOCUMENTS

| | | |
|---|---|---|
| 5,868,762 A | 2/1999 | Cragg et al. |
| 5,873,891 A | 2/1999 | Sohn |
| 5,879,357 A | 3/1999 | Heaton et al. |
| 5,897,574 A | 4/1999 | Bonutti |
| 5,899,911 A | 5/1999 | Carter |
| 5,899,921 A | 5/1999 | Caspari et al. |
| 5,904,679 A | 5/1999 | Clayman |
| 5,904,696 A | 5/1999 | Rosenman |
| 5,908,428 A | 6/1999 | Scirica et al. |
| 5,919,198 A | 7/1999 | Graves, Jr. et al. |
| 5,919,202 A | 7/1999 | Yoon |
| 5,921,986 A | 7/1999 | Bonutti |
| 5,928,252 A | 7/1999 | Steadman et al. |
| 5,931,844 A | 8/1999 | Thompson et al. |
| 5,944,739 A | 8/1999 | Zlock et al. |
| 5,948,001 A | 9/1999 | Larsen |
| 5,948,002 A | 9/1999 | Bonutti |
| 5,954,057 A | 9/1999 | Li |
| 5,954,747 A | 9/1999 | Clark |
| 5,964,732 A | 10/1999 | Willard |
| 5,971,447 A | 10/1999 | Steck, III |
| 6,010,514 A | 1/2000 | Burney et al. |
| 6,011,525 A | 1/2000 | Piole |
| 6,030,393 A | 2/2000 | Corlew |
| 6,033,430 A | 3/2000 | Bonutti |
| 6,036,701 A | 3/2000 | Rosenman |
| 6,048,351 A | 4/2000 | Gordon et al. |
| 6,053,908 A | 4/2000 | Crainich et al. |
| 6,056,722 A | 5/2000 | Jayaraman |
| 6,056,772 A | 5/2000 | Bonutti |
| 6,068,648 A | 5/2000 | Cole et al. |
| 6,080,167 A | 6/2000 | Lyell |
| 6,086,608 A | 7/2000 | Ek et al. |
| 6,110,183 A | 8/2000 | Cope |
| 6,117,160 A | 9/2000 | Bonutti |
| 6,117,161 A | 9/2000 | Li et al. |
| 6,120,539 A | 9/2000 | Eldridge et al. |
| 6,139,555 A | 10/2000 | Hart et al. |
| RE36,974 E | 11/2000 | Bonutti |
| 6,143,006 A | 11/2000 | Chan |
| 6,152,935 A | 11/2000 | Kammerer et al. |
| 6,159,234 A | 12/2000 | Bonutti et al. |
| 6,200,329 B1 | 3/2001 | Fung et al. |
| 6,206,895 B1 | 3/2001 | Levinson |
| 6,228,096 B1 | 5/2001 | Marchand |
| 6,258,124 B1 | 7/2001 | Darois et al. |
| 6,261,302 B1 | 7/2001 | Voegele et al. |
| 6,270,530 B1 | 8/2001 | Eldridge et al. |
| 6,280,460 B1 | 8/2001 | Bolduc et al. |
| 6,290,711 B1 | 9/2001 | Caspari et al. |
| 6,312,448 B1 | 11/2001 | Bonutti |
| 6,319,263 B1 | 11/2001 | Levinson |
| 6,322,112 B1 | 11/2001 | Duncan |
| 6,332,889 B1 | 12/2001 | Sancoff et al. |
| 6,398,795 B1 | 6/2002 | McAlister et al. |
| 6,425,900 B1 | 7/2002 | Knodel et al. |
| 6,428,562 B2 | 8/2002 | Bonutti |
| 6,436,107 B1 | 8/2002 | Wang et al. |
| 6,461,355 B2 | 10/2002 | Svejkovsky et al. |
| 6,482,235 B1 | 11/2002 | Lambrecht et al. |
| 6,488,691 B1 | 12/2002 | Carroll et al. |
| 6,491,707 B2 | 12/2002 | Makower et al. |
| 6,494,888 B1 | 12/2002 | Laufer et al. |
| 6,500,195 B2 | 12/2002 | Bonutti |
| 6,506,190 B1 | 1/2003 | Walshe |
| 6,506,196 B1 | 1/2003 | Laufer |
| 6,517,569 B2 | 2/2003 | Mikus et al. |
| 6,527,702 B2 | 3/2003 | Whalen et al. |
| 6,527,794 B1 | 3/2003 | McDevitt et al. |
| 6,530,932 B1 | 3/2003 | Swayze et al. |
| 6,533,796 B1 | 3/2003 | Sauer et al. |
| 6,547,725 B1 | 4/2003 | Paolitto et al. |
| 6,551,328 B2 | 4/2003 | Kortenbach |
| 6,551,333 B2 | 4/2003 | Kuhns et al. |
| 6,565,578 B1 | 5/2003 | Peifer et al. |
| 6,569,187 B1 | 5/2003 | Bonutti et al. |
| 6,572,626 B1 | 6/2003 | Knodel et al. |
| 6,572,635 B1 | 6/2003 | Bonutti |
| 6,572,653 B1 | 6/2003 | Simonson |
| 6,592,609 B1 | 7/2003 | Bonutti |
| 6,596,013 B2 | 7/2003 | Yang et al. |
| 6,626,913 B1 | 9/2003 | McKinnon et al. |
| 6,626,916 B1 | 9/2003 | Yeung et al. |
| 6,626,919 B1 | 9/2003 | Swanstrom |
| 6,629,534 B1 | 10/2003 | St. Goar et al. |
| 6,641,592 B1 | 11/2003 | Sauer et al. |
| 6,656,182 B1 | 12/2003 | Hayhurst |
| 6,660,023 B2 | 12/2003 | McDevitt et al. |
| 6,663,589 B1 | 12/2003 | Halevy |
| 6,663,639 B1 | 12/2003 | Laufer et al. |
| 6,699,263 B2 | 3/2004 | Cope |
| 6,706,047 B2 | 3/2004 | Trout et al. |
| 6,709,493 B2 | 3/2004 | DeGuiseppi et al. |
| 6,715,804 B2 | 4/2004 | Beers |
| 6,719,709 B2 | 4/2004 | Whalen et al. |
| 6,730,112 B2 | 5/2004 | Levinson |
| 6,736,823 B2 | 5/2004 | Darois et al. |
| 6,736,854 B2 | 5/2004 | Vadurro et al. |
| 6,740,098 B2 | 5/2004 | Abrams et al. |
| 6,767,037 B2 | 7/2004 | Wenstrom, Jr. |
| 6,770,076 B2 | 8/2004 | Foerster |
| 6,773,438 B1 | 8/2004 | Knodel et al. |
| 6,773,441 B1 | 8/2004 | Laufer et al. |
| 6,790,213 B2 | 9/2004 | Cherok et al. |
| 6,802,846 B2 | 10/2004 | Hauschild et al. |
| 6,821,282 B2 | 11/2004 | Perry et al. |
| 6,821,285 B2 | 11/2004 | Laufer et al. |
| 6,821,291 B2 | 11/2004 | Bolea et al. |
| 6,835,200 B2 | 12/2004 | Laufer et al. |
| 6,905,475 B2 | 6/2005 | Hauschild et al. |
| 6,908,473 B2 | 6/2005 | Skiba et al. |
| 6,926,732 B2 | 8/2005 | Derus et al. |
| 6,951,565 B2 | 10/2005 | Keane et al. |
| 6,986,775 B2 | 1/2006 | Morales et al. |
| 6,991,596 B2 | 1/2006 | Whalen et al. |
| 6,991,647 B2 | 1/2006 | Jadhav |
| 6,997,940 B2 | 2/2006 | Bonutti |
| 7,001,327 B2 | 2/2006 | Whalen et al. |
| 7,011,688 B2 | 3/2006 | Gryska et al. |
| 7,015,253 B2 | 3/2006 | Escandon et al. |
| 7,041,111 B2 * | 5/2006 | Chu .............................. 606/144 |
| 7,048,698 B2 | 5/2006 | Whalen et al. |
| 7,048,747 B2 | 5/2006 | Arcia et al. |
| 7,060,077 B2 | 6/2006 | Gordon et al. |
| 7,081,126 B2 | 7/2006 | McDevitt et al. |
| 7,083,638 B2 | 8/2006 | Foerster |
| 7,087,073 B2 | 8/2006 | Bonutti |
| 7,089,064 B2 | 8/2006 | Manker et al. |
| 7,090,690 B2 | 8/2006 | Foerster et al. |
| 7,093,601 B2 | 8/2006 | Manker et al. |
| 7,105,004 B2 | 9/2006 | Dicesare et al. |
| 7,108,655 B2 | 9/2006 | Whalen et al. |
| 7,141,038 B2 | 11/2006 | Whalen et al. |
| 7,153,314 B2 | 12/2006 | Laufer et al. |
| 7,179,225 B2 | 2/2007 | Shluzas |
| 7,226,558 B2 | 6/2007 | Nieman et al. |
| 7,232,448 B2 | 6/2007 | Battles et al. |
| 7,288,063 B2 | 10/2007 | Petros et al. |
| 7,303,108 B2 | 12/2007 | Shelton, IV |
| 7,320,701 B2 | 1/2008 | Haut et al. |
| 7,322,974 B2 | 1/2008 | Swoyer et al. |
| 7,326,221 B2 | 2/2008 | Sakamoto et al. |
| 7,334,822 B1 | 2/2008 | Hines, Jr. |
| 7,340,300 B2 | 3/2008 | Christopherson et al. |
| 7,399,304 B2 | 7/2008 | Gambale et al. |
| 7,402,166 B2 | 7/2008 | Fiegl |
| 7,416,554 B2 | 8/2008 | Lam et al. |
| 7,417,175 B2 | 8/2008 | Oda et al. |
| 7,481,771 B2 | 1/2009 | Fonseca et al. |
| 7,553,317 B2 | 6/2009 | Weisenburgh, II et al. |
| 7,608,108 B2 | 10/2009 | Bhatnagar et al. |
| 7,658,311 B2 | 2/2010 | Boudreaux |
| 7,674,275 B2 | 3/2010 | Martin et al. |
| 7,727,248 B2 | 6/2010 | Smith et al. |

(56) References Cited

U.S. PATENT DOCUMENTS

| | | |
|---|---|---|
| 2001/0044639 A1 | 11/2001 | Levinson |
| 2002/0095154 A1 | 7/2002 | Atkinson et al. |
| 2002/0128684 A1 | 9/2002 | Foerster |
| 2002/0161382 A1 | 10/2002 | Neisz et al. |
| 2002/0193809 A1 | 12/2002 | Meade |
| 2003/0109769 A1 | 6/2003 | Lowery et al. |
| 2003/0191497 A1* | 10/2003 | Cope ........................ 606/215 |
| 2003/0204195 A1 | 10/2003 | Keane et al. |
| 2003/0236535 A1 | 12/2003 | Onuki et al. |
| 2004/0030217 A1 | 2/2004 | Yeung et al. |
| 2004/0043052 A1 | 3/2004 | Hunter et al. |
| 2004/0078046 A1 | 4/2004 | Barzell et al. |
| 2004/0122456 A1* | 6/2004 | Saadat et al. .................. 606/157 |
| 2004/0193191 A1 | 9/2004 | Starksen et al. |
| 2004/0193194 A1 | 9/2004 | Laufer et al. |
| 2004/0194790 A1 | 10/2004 | Laufer et al. |
| 2004/0243178 A1 | 12/2004 | Haut et al. |
| 2004/0243179 A1 | 12/2004 | Foerster |
| 2004/0243180 A1 | 12/2004 | Donnelly |
| 2004/0243227 A1 | 12/2004 | Starksen et al. |
| 2004/0260345 A1 | 12/2004 | Foerster |
| 2005/0055087 A1 | 3/2005 | Starksen |
| 2005/0065550 A1 | 3/2005 | Starksen et al. |
| 2005/0107811 A1 | 5/2005 | Starksen et al. |
| 2005/0107812 A1 | 5/2005 | Starksen et al. |
| 2005/0154401 A1 | 7/2005 | Weldon et al. |
| 2005/0165272 A1 | 7/2005 | Okada et al. |
| 2005/0177181 A1 | 8/2005 | Kagan et al. |
| 2005/0203344 A1 | 9/2005 | Orban, III et al. |
| 2005/0203550 A1 | 9/2005 | Laufer et al. |
| 2005/0216078 A1 | 9/2005 | Starksen et al. |
| 2005/0267405 A1 | 12/2005 | Shah |
| 2005/0273138 A1 | 12/2005 | Starksen et al. |
| 2006/0025750 A1 | 2/2006 | Starksen et al. |
| 2006/0025784 A1 | 2/2006 | Starksen et al. |
| 2006/0025789 A1 | 2/2006 | Laufer et al. |
| 2006/0025819 A1 | 2/2006 | Nobis et al. |
| 2006/0030884 A1 | 2/2006 | Yeung et al. |
| 2006/0058817 A1 | 3/2006 | Starksen et al. |
| 2006/0089646 A1 | 4/2006 | Bonutti |
| 2006/0167477 A1 | 7/2006 | Arcia et al. |
| 2006/0265042 A1 | 11/2006 | Catanese, III et al. |
| 2006/0282081 A1 | 12/2006 | Fanton et al. |
| 2007/0049929 A1 | 3/2007 | Catanese, III |
| 2007/0049970 A1 | 3/2007 | Belef et al. |
| 2007/0060931 A1 | 3/2007 | Hamilton et al. |
| 2007/0088362 A1 | 4/2007 | Bonutti |
| 2007/0112385 A1 | 5/2007 | Conlon |
| 2007/0142846 A1 | 6/2007 | Catanese, III et al. |
| 2007/0173888 A1 | 7/2007 | Gertner et al. |
| 2007/0260259 A1 | 11/2007 | Fanton et al. |
| 2008/0009888 A1 | 1/2008 | Ewers et al. |
| 2008/0021445 A1 | 1/2008 | Elmouelhi et al. |
| 2008/0033488 A1 | 2/2008 | Catanese, III et al. |
| 2008/0039874 A1 | 2/2008 | Catanese, III et al. |
| 2008/0039894 A1 | 2/2008 | Catanese, III et al. |
| 2008/0045978 A1 | 2/2008 | Kuhns et al. |
| 2008/0058710 A1 | 3/2008 | Wilk |
| 2008/0065120 A1 | 3/2008 | Zannis et al. |
| 2008/0082113 A1 | 4/2008 | Bishop et al. |
| 2008/0086172 A1 | 4/2008 | Martin et al. |
| 2008/0091220 A1 | 4/2008 | Chu |
| 2008/0091237 A1 | 4/2008 | Schwartz et al. |
| 2008/0119874 A1 | 5/2008 | Merves |
| 2008/0154378 A1 | 6/2008 | Pelo |
| 2008/0195145 A1 | 8/2008 | Bonutti et al. |
| 2008/0208220 A1 | 8/2008 | Shiono et al. |
| 2010/0010631 A1 | 1/2010 | Otte et al. |
| 2010/0114162 A1 | 5/2010 | Bojarski et al. |
| 2010/0286106 A1 | 11/2010 | Gat et al. |
| 2010/0286679 A1 | 11/2010 | Hoey et al. |

FOREIGN PATENT DOCUMENTS

| | | |
|---|---|---|
| EP | 0632999 | 1/1995 |
| EP | 1016377 | 7/2000 |
| EP | 1082941 | 3/2005 |
| EP | 1006909 | 1/2007 |
| EP | 1852071 | 11/2007 |
| EP | 0464480 | 1/2008 |
| EP | 1670361 | 4/2008 |
| EP | 1884198 | 6/2008 |
| EP | 1884199 | 6/2008 |
| EP | 1331886 | 12/2008 |
| FR | 2750031 | 6/1996 |
| JP | 58036559 | 3/1983 |
| RU | 2062121 | 6/1996 |
| RU | 2112571 | 6/1998 |
| RU | 2128012 | 3/1999 |
| RU | 2221501 | 1/2004 |
| SU | 0825094 | 4/1981 |
| WO | WO 92/10142 | 6/1992 |
| WO | WO 93/04727 | 3/1993 |
| WO | WO 93/15664 | 8/1993 |
| WO | WO 0230335 | 4/2002 |
| WO | WO 03/039334 | 5/2003 |
| WO | WO03/077772 | 9/2003 |
| WO | WO2004019787 | 3/2004 |
| WO | WO2004017845 | 4/2004 |
| WO | WO2004030569 | 4/2004 |
| WO | WO2004103189 | 12/2004 |
| WO | WO2007064906 | 6/2007 |
| WO | WO2007053516 | 10/2007 |
| WO | WO2008006084 | 1/2008 |
| WO | WO2008043044 | 4/2008 |
| WO | WO2008443917 | 4/2008 |
| WO | WO2009009617 | 1/2009 |
| WO | WO2010011832 | 1/2010 |

OTHER PUBLICATIONS

Rudolf Hartung, et al., "Instrumentelle Therapie der benignen Prostatahyperplasie", Medizin, Deutsches Arzteblatt 97, Heft 15, Apr. 14, 2000.

Klaus Hofner, et al., "Operative Therapie des benignen Prostatasyndroms", Medizin, Dtsch Arztebl 2007; 104(36):A 2424-9.

R. Hubmann, "Geschichte der transurethralen Prostataeingriffe", Geschichte der Medizin, Urologe [B] 2000 40:152-160.

U. Jonas, et al., "Benigne Prostatahyperplasie", Der Urologe 2006—[Sonderheft] 45:134-144.

O.A. Bacharova, et al., "The Effect of Rhodiolae Rosea Extract on Incidence Rate of Superficial Bladder Carcinoma Relapses", Kozin 1995.

S. Kruck, et al., "Aktuelle Therapiemoglichkeiten des Benignen Prostata-Syndroms", J Urol Urogynakol 2009; 16 (1):19-22.

Osamu Miyake, "Medical Examination and Treatment for BPH", Pharma Med vol. 22, No. 3, 2004, p. 97-103.

Ohashi Teruhisa, "Urinary Dysfunction by Lower Urinary Tract Obstruction in Male", Pharma Medica vol. 8, No. 8, p. 35-39.

O. Reich, et al. "Benignes Prostatasyndrom (BPS)", Der Urologe A Issue vol. 45, No. 6, Jun. 2006, p. 769-782.

Daito Takashi, "Low-Invasive Treatment for BPH", Medico vol. 34, No. 10, p. 366-369.

Trapeznikov et al., "New Technologies in the Treatment of Benign Prostatic Hyperplasia", Urologia Nefrol (Mosk) Jul.-Aug. 1996, (4):41-47.

Koyanagi Tomohiko, et al., "Surgery View of 21st Century", Urological Surgery, vol. 84, No. 1, p. 47-53.

Borzhievski, et al., "Tactics of the Surgical Treatment of Patients With Prostatic Adenoma and Acute Urinary Retention", Urologia Nefrol (Mosk), Jan.-Feb. 1987, (1):39-43.

Sharp, Howard T., M.D., et al., "Instruments and Methods—The 4-S Modification of the Roeder Knot: How to Tie It", Obstetrics & Gynecology, p. 1004-1006, vol. 90, No. 6, Dec. 1997.

(56) References Cited

OTHER PUBLICATIONS

P. Schauer et al., "New applications for endoscopy: the emerging field of endoluminal and transgastric bariatric surgery," Surgical Endoscopy, Accepted Jun. 7, 2006.

Yeung, Jeff, "Treating Urinary Stress Incontinence Without Incision With Endoscopic Suture Anchor and Approximating Device," Aleeva Medical, Inc., 2007.

* cited by examiner

CONTINUOUS INDENTATION LATERAL LOBE APPARATUS AND METHOD

CROSS-REFERENCES TO RELATED APPLICATIONS

This application is a continuation-in-part of: 1) copending U.S. patent application Ser. No. 12/852,243, filed Aug. 6, 2010; 2) copending U.S. patent application Ser. No. 12/512,674, filed Jul. 30, 2009 which claims the benefit of Provisional Application Ser. No. 61/084,937; 3) copending U.S. patent application Ser. No. 11/775,162, filed Jul. 9, 2007: 4) copending U.S. patent application Ser. No. 11/671,914, filed Feb. 6, 2007; 5) copending U.S. patent application Ser. No. 11/492,690, filed on Jul. 24, 2006; 6) copending U.S. patent application Ser. No. 11/833,660, filed on Aug. 3, 2007, which is a continuation of U.S. patent application Ser. No. 11/318,246, filed on Dec. 20, 2005; and 7) copending U.S. patent application Ser. No. 11/838,036 filed on Aug. 13, 2007, which is a continuation of U.S. patent application Ser. No. 11/134,870 filed on May 20, 2005; the entire disclosures of each of which are expressly incorporated herein by reference.

FIELD OF THE INVENTION

The present invention relates generally to medical devices and methods, and more particularly to systems and associated methods for manipulating or retracting tissues and anatomical or other structures within the body of human or animal subjects for the purpose of treating diseases or disorders.

One example of a condition where it is desirable to lift, compress or otherwise remove a pathologically enlarged tissue is Benign Prostatic Hyperplasia (BPH). BPH is one of the most common medical conditions that affect men, especially elderly men. It has been reported that, in the United States, more than half of all men have histopathologic evidence of BPH by age 60 and, by age 85, approximately 9 out of 10 men suffer from the condition. Moreover, the incidence and prevalence of BPH are expected to increase as the average age of the population in developed countries increases.

The prostate gland enlarges throughout a man's life. In some men, the prostatic capsule around the prostate gland may prevent the prostate gland from enlarging further. This causes the inner region of the prostate gland to squeeze the urethra. This pressure on the urethra increases resistance to urine flow through the region of the urethra enclosed by the prostate. Thus the urinary bladder has to exert more pressure to force urine through the increased resistance of the urethra. Chronic over-exertion causes the muscular walls of the urinary bladder to remodel and become stiffer. This combination of increased urethral resistance to urine flow and stiffness and hypertrophy of urinary bladder walls leads to a variety of lower urinary tract symptoms (LUTS) that may severely reduce the patient's quality of life. These symptoms include weak or intermittent urine flow while urinating, straining when urinating, hesitation before urine flow starts, feeling that the bladder has not emptied completely even after urination, dribbling at the end of urination or leakage afterward, increased frequency of urination particularly at night, urgent need to urinate etc.

In addition to patients with BPH, LUTS may also be present in patients with prostate cancer, prostate infections, and chronic use of certain medications (e.g. ephedrine, pseudoephedrine, phenylpropanolamine, antihistamines such as diphenhydramine, chlorpheniramine etc.) that cause urinary retention especially in men with prostate enlargement.

Although BPH is rarely life threatening, it can lead to numerous clinical conditions including urinary retention, renal insufficiency, recurrent urinary tract infection, incontinence, hematuria, and bladder stones.

In developed countries, a large percentage of the patient population undergoes treatment for BPH symptoms. It has been estimated that by the age of 80 years, approximately 25% of the male population of the United States will have undergone some form of BPH treatment. At present, the available treatment options for BPH include watchful waiting, medications (phytotherapy and prescription medications), surgery and minimally invasive procedures.

For patients who choose the watchful waiting option, no immediate treatment is provided to the patient, but the patient undergoes regular exams to monitor progression of the disease. This is usually done on patients that have minimal symptoms that are not especially bothersome.

Surgical procedures for treating BPH symptoms include Transurethal Resection of Prostate (TURP), Transurethral Electrovaporization of Prostate (TVP), Transurethral Incision of the Prostate (TUIP), Laser Prostatectomy and Open Prostatectomy.

Minimally invasive procedures for treating BPH symptoms include Transurethral Microwave Thermotherapy (TUMT), Transurethral Needle Ablation (TUNA), Interstitial Laser Coagulation (ILC), and Prostatic Stents.

The most effective current methods of treating BPH carry a high risk of adverse effects. These methods and devices either require general or spinal anesthesia or have potential adverse effects that dictate that the procedures be performed in a surgical operating room, followed by a hospital stay for the patient. The methods of treating BPH that carry a lower risk of adverse effects are also associated with a lower reduction in the symptom score. While several of these procedures can be conducted with local analgesia in an office setting, the patient does not experience immediate relief and in fact often experiences worse symptoms for weeks after the procedure until the body begins to heal. Additionally all device approaches require a urethral catheter placed in the bladder, in some cases for weeks. In some cases catheterization is indicated because the therapy actually causes obstruction during a period of time post operatively, and in other cases it is indicated because of post-operative bleeding and potentially occlusive clot formation. While drug therapies are easy to administer, the results are suboptimal, take significant time to take effect, and often entail undesired side effects.

There have been advances in developing minimally invasive devices and methods for cosmetic lifting and repositioning of tissues. For example, approaches have been proposed to displace and/or compress lobes of a prostate gland to receive pressure on and provide a less obstructed path through a urethra.

There remains, however, a need for the development of new devices and methods that can be used for various procedures where it is desired to lift, compress, support or reposition the lobes of a prostate. In particular, there is a need for alternative apparatus and treatment approaches for the purpose of creating a continuous defect or indentation along a length of the prostate. Various structures ensuring an effective creation of such an indentation are needed.

The present disclosure addresses these and other needs.

SUMMARY

Briefly and in general terms, the present invention is directed towards an apparatus and method for deploying an anchor assembly within a patient's body to accomplish the creation of a continuous defect or indentation of a lobe of a prostate to lesson obstruction or constriction of the urethra. A delivery device is provided to access the anatomy targeted for the interventional procedure. The delivery device facilitates the implantation of the anchor assembly in a manner accomplishing the creation of the continuous defect or indentation. This treatment can be performed along with drug elution techniques for shrinking the prostate.

The delivery apparatus of the present disclosure includes various subassemblies which are mobilized via an actuator or other manually accessible structure. The operation of the subassemblies is coordinated and synchronized to ensure accurate and precise implantation of an anchor assembly. In one embodiment, the delivery device is embodied in a tissue approximation assembly.

In one particular aspect, the present disclosure is directed towards a delivery device including a pair of extendable needles which accomplishes the delivery of a pair of distal anchor assembly components at a first location within a patient's body and the delivery of a pair of proximal anchor assembly components at a second location within the patient. The device also accomplishes imparting tension during delivery to a connector to hold it while implanting the proximal anchor in situ. The procedure can be viewed employing a scope inserted in the device. Also, the delivery device can be sized and shaped to be compatible with and placed inside a sheath up to 24 F, preferably a 19 F sheath or smaller. The sheath can further include a distal end portion including an overmolding providing an atraumatic surface. Further, it is contemplated that an over jacket can be attached or form part of the sheath, where the over jacket joins a drainage lumen to the sheath.

The anchor assembly can be configured to accomplish approximating, retracting, lifting, compressing, supporting or repositioning tissue within the body of a human or animal subject. Moreover, the apparatus configured to deploy the anchor assembly as well as the anchor assembly itself are configured to complement and cooperate with body anatomy. Further, the anchor assembly can be coated or imbedded with therapeutic or diagnostic substances, in particular Botulinum toxin, or a silver ion coating or such substances can be introduced into or near an interventional site by the anchor deployment device or other structure.

In various approaches, the anchor can include one or more distal anchors connected to one or more proximal anchors by a connector. In one approach, the distal anchors have a body with a tail and the proximal anchors can include a pair of spaced members which are configured to capture and deform the connector there between and prevent the connector from disengaging from the anchor device once engaged. The mechanism of connector attachment and strength of the assembly is a combination of compression of the connector between deformable structure of the anchor as well as disruption of the connector surface by the anchor. The deformable structure provides surface contact and focuses the compressive forces that cause the connector to conform about the anchor.

Various different anchor structures are contemplated. The anchor can include a single circular loop made from flexible material or can define a coil which can be extended and flattened for delivery. Further, the anchor can define an umbrella structure which is held closed during delivery and permitted to expand after placement at an implant site or a structure which expands in width as it contracts in length. Moreover, the anchors can embody dual struts or corkscrew structure and include a body for providing longer tissue compression lengths or can additionally include a main body with a plurality of shape set wings along its length.

In yet further contemplated approaches, the anchor includes a proximal portion which is sized and shaped to create a continuous defect or indentation on the lobe of the prostate. The anchor can be equipped with a repeating component that can assume a folded structure at a proximal end portion. The anchors can additionally or alternatively include clips intended to retain a bar that creates the continuing indentation or the anchor can be embodied in an elongate needle or trocar having a preset curved configuration.

Various alternative methods of use are also contemplated. The disclosed apparatus can be used to improve flow of a body fluid through a body lumen, modify the size or shape of a body lumen or cavity, treat prostate enlargement, treat urinary incontinence, support or maintain positioning of a tissue, close a tissue wound, organ or graft, perform a cosmetic lifting or repositioning procedure, form anastomotic connections, and/or treat various other disorders where a natural or pathologic tissue or organ is pressing on or interfering with an adjacent anatomical structure. Also, the present approach has a myriad of other potential surgical, therapeutic, cosmetic or reconstructive applications, such as where a tissue, organ, graft or other material requires approximately, retracting, lifting, repositioning, compression or support.

In a specific application, the disclosed apparatus are contemplated to be employed to create a continuous defect or indentation in a lobe of a prostate. In one aspect, an anchoring device housed within a delivery device is inserted into a prosthetic urethra transurethrally and the delivery device is employed to compress or displace the prostatic lobe. The anchor is then used to create the defect/indentation and to maintain the lobe in the compressed or displaced configuration.

Other features and advantages of the present invention will become apparent from the following detailed description, taken in conjunction with the accompanying drawings, which illustrate, by way of example, the principles of the invention.

DETAILED DESCRIPTION OF THE PREFERRED EMBODIMENTS

Figure 1:
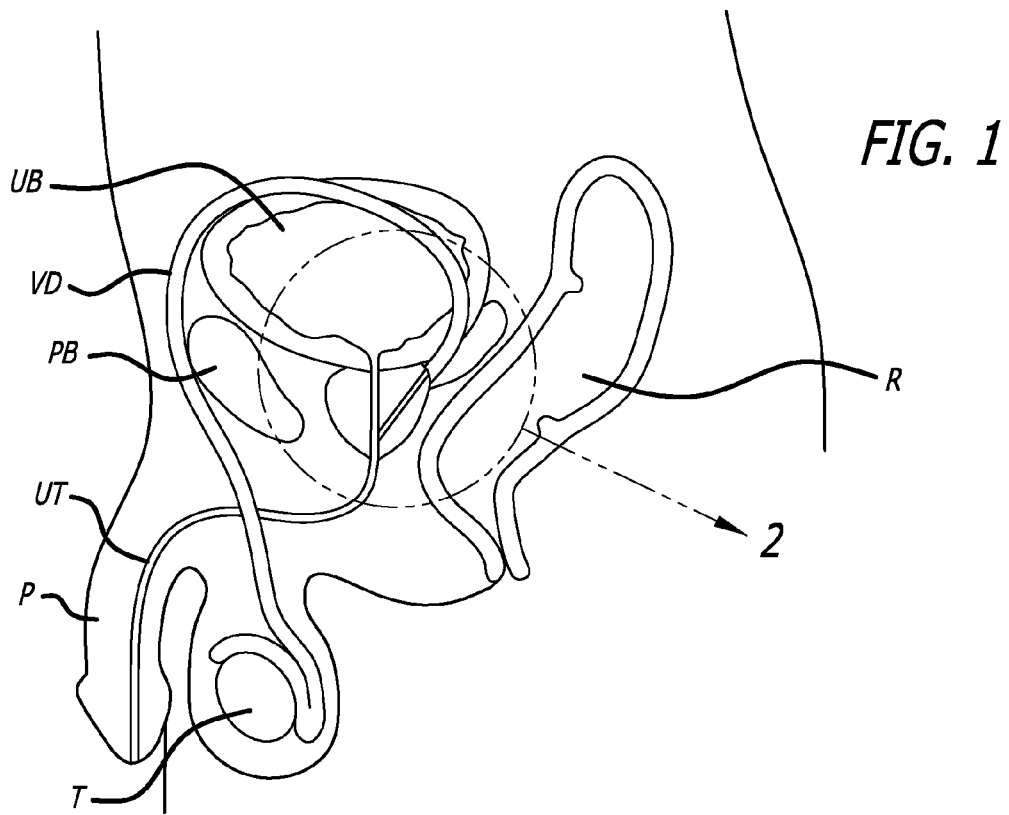
FIG. 1 is a cross-sectional view, depicting anatomy surrounding a prostate in a human subject.
Figure 2:
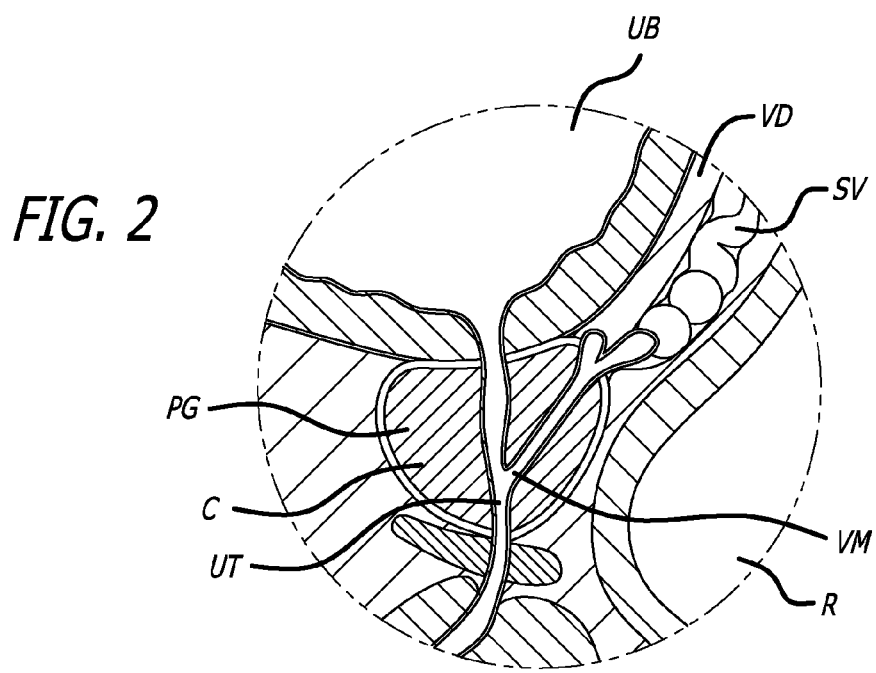
FIG. 2 is an enlarged cross-sectional view, depicting anatomy surrounding a prostate.
Figure 3:
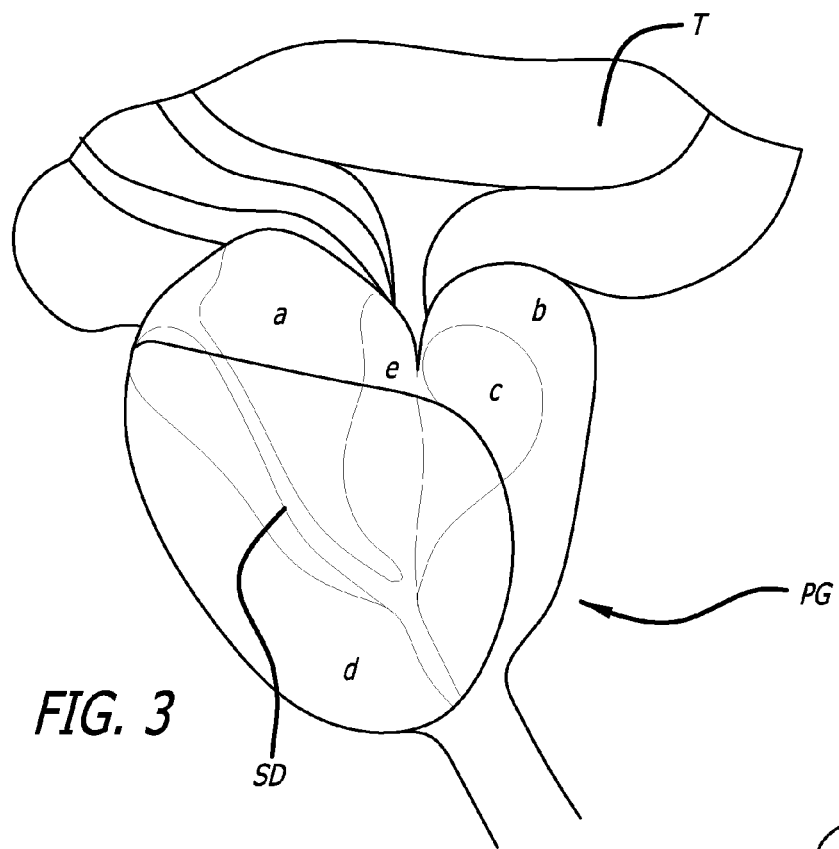
FIG. 3 is a schematic view, depicting prostatic anatomy zones.

Turning now to the figures, which are provided by way of example and not limitation, the present disclosure is directed to a device configured to deliver an anchor assembly within a patient's body for treatment purposes. The disclosed apparatus can be employed for various medical purposes including but not limited to retracting, lifting, compressing, approximating, supporting or repositioning tissues, organs, anatomical structures, grafts or other material found within a patient's body. Such tissue manipulation is intended to facilitate the treatment of diseases or disorders such as the formation of a continuous defect or indentation in a lobe of a prostate. The continuous defect or indentation can be an increase of a luminal opening of the urethra extending an entire length of the prostatic urethra. Further, the continuous defect or indentation can extend from the verumontanum to the bladder neck or simply be greater than a length of a structure or anchor placed to create this effect in the urethra (such as thirty percent longer in one or more directions parallel to the implanted structure).

In an aspect of the present disclosure, one portion of an anchor assembly or implant is positioned and implanted against a first section of anatomy. A second portion of the anchor assembly or implant is then positioned and implanted adjacent a second section of anatomy for the purpose of creating a continuous defect or indentation in anatomy as well as for the purpose of retracting, lifting, compressing, approximating, supporting or repositioning the first section of anatomy with respect to the second section of anatomy. It is also to be recognized that both a first and second portion of the anchor assembly can be configured to accomplish the desired retracting, lifting, compressing, approximating, supporting or repositioning of anatomy due to tension supplied during delivery via a connector assembly affixed to the first and second portions of the anchor assembly or implant.

With reference to FIGS. 1-4, various features of urological anatomy of a human subject are presented. The prostate gland PG is a walnut-sized muscular gland located adjacent the urinary bladder UB. The urethra UT runs through the prostate gland PG. The prostate gland PG secretes fluid that protects and nourishes sperm. The prostate also contracts during ejaculation of sperm to expel semen and to provide a valve to keep urine out of the semen. A capsule C surrounds the prostate gland PG.

The urinary bladder UB holds urine. The vas deferentia VD define ducts through which semen is carried and the seminal vesicles SV secrete seminal fluid. The rectum R is the end segment of the large intestine and through which waste is dispelled. The urethra UT carries both urine and semen out of the body. Thus, the urethra is connected to the urinary bladder UB and provides a passageway to the vas deferentia VD and seminal vesicles SV.

Further, the trigone T (See FIG. 3) is a smooth triangular region of the bladder. It is sensitive to expansion and signals the brain when the urinary bladder UB is full. The verumontanum VM is a crest in the wall of the urethra UT where the seminal ducts enter. The prostatic urethra is the section of the urethra UT which extends through the prostate.

Figure 4:
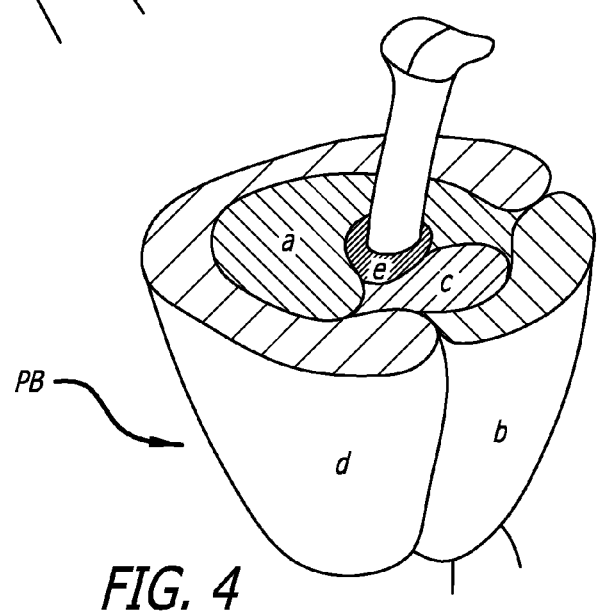
FIG. 4 is a schematic cross-sectional view, depicting further details of the anatomy zones shown in FIG. 3.

The prostate gland can be classified by zones or described by referring to its lobes (see FIG. 4). Whereas the zone classification is typically used in pathology, the lobe classification is more often used in anatomy. The central zone (a) of a prostate gland PG is about 25% of a normal prostate and this zone surrounds the ejaculating ducts. There is some prevalence of benign prostate hyperplasia in the transition zone. The fibromuscular zone (b) is usually devoid of glandular components and as its name suggests, is composed of only muscle and fibrous tissue. The transitional zone (c) generally overlays the proximal urethra and is the region of the gland that grows throughout life. Also, this lobe is often associated with the condition of benign prostatic enlargement. Finally, the peripheral zone (d) is the sub-capsular portion of the posterior aspect of the prostate gland that surrounds the distal urethra.

The lobe characterization is different from the zone characterization, but there is some overlap. The anterior lobe is devoid of glandular tissue and is completely formed of fibromuscular tissue. This lobe thus roughly corresponds to the anterior portion of the transitional zone (c). The posterior lobe roughly corresponds to the peripheral zone (d) and can be palpated through the rectum during a digital rectal exam. The posterior lobe is the site of 70-80% of prostatic cancers. The lateral lobe is the main mass of the prostate and is separated by the urethra. It has been described as spanning all zones. Lastly, the median lobe roughly corresponds to part of the central zone. It varies greatly in size and in some cases is devoid of glandular tissue.

A large or enlarged median lobe can act as a ball valve, blocking the bladder neck. Various approaches are contemplated to address such a condition. Thus, it is contemplated that the median lobe can be compressed, displaced and/or retracted to eliminate or decrease the blocking of the bladder neck.

Figure 5:
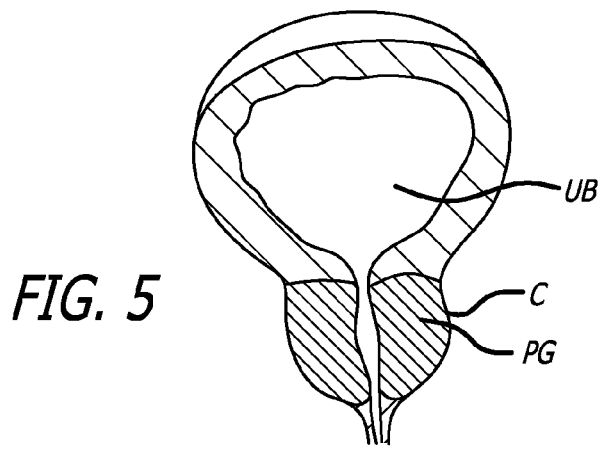
FIG. 5 is a cross-sectional view, depicting a normal prostate.
Figure 6:
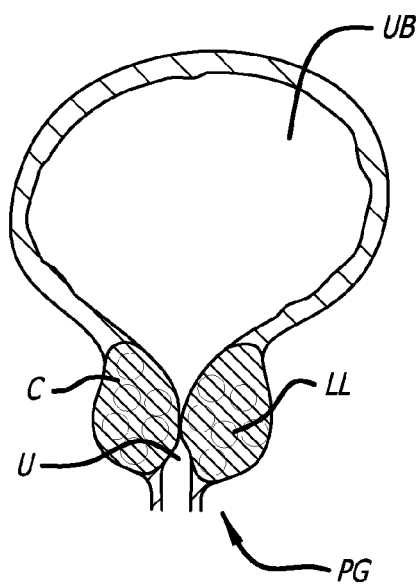
FIG. 6 is a cross-sectional view, depicting a prostate with enlarged lateral lobes.
Figure 7:
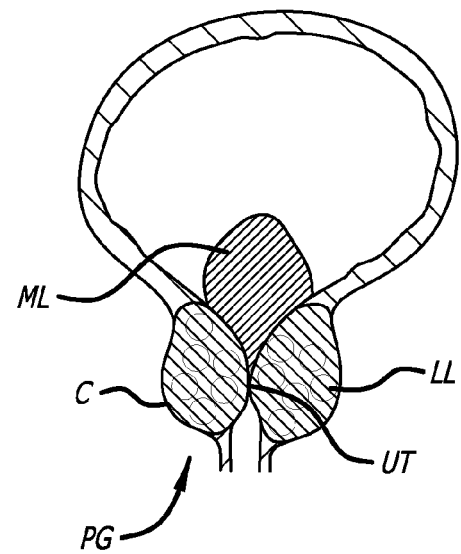
FIG. 7 is a cross-sectional view, depicting a prostate with enlarged lateral lobes and an enlarged median lobe.

Turning now to FIGS. 5-7, there are shown various prostate glands in cross-section. FIG. 5 depicts the urinary bladder UB and prostate gland PG of a healthy subject. FIG. 6 illustrates an individual with a prostate having enlarged lateral lobes LL and FIG. 7 depicts a subject suffering from both enlarged lateral lobes LL and an enlarged median lobe ML. It is to be appreciated that such enlarged anatomy impinges on the urethra UT and affects normal functioning. The following devices and approaches are intended to be employed to free up a path through the prostatic urethra. It is contemplated that such a path can be provided by forming one or more permanent valleys along the prostatic urethra and/or creating a continuous indentation in the prostatic urethra.

The tissue approximation anchor is designed to be useable in an office environment (in contrast to requiring a hospital environment) with a delivery tool. The delivery tool is used through a 19 Fr sheath in one preferred embodiment, while in another embodiment a sheath size of 21 F is employed. Additionally, the material selection and construction of the tissue approximation anchor still allows for a subsequent TURP procedure to be performed, if necessary, on the prostate. In this suture-based, tissue approximation technique, a needle delivery mechanism is used to implant a distal component of an anchor and attached suture or connector. Once the distal anchor component has been deployed, the needle or needles are retracted and the connector tensioned, the proximal anchor is then deployed.

Referring now to FIGS. 8A-D, there is shown one embodiment of a delivery device 100. This device is configured to include structure that is capable of both gaining access to an interventional site as well as implanting and/or assembling one or more anchor assemblies or implants within a patient's body. The device is further contemplated to be compatible for use with a 19 F sheath. The device additionally includes structure configured to receive a remote viewing device (e.g., an endoscope) so that the steps being performed at the interventional site can be observed.

Prior to use of the present device 100, a patient typically undergoes a five day regiment of antibiotics. A local anesthesia can be employed for the interventional procedure. A combination of an oral analgesic with a sedative or hypnotic component can be ingested by the patient. Moreover, topical anesthesia such as lidocaine liquids or gel can be applied to the bladder and urethra.

The anchor delivery device 100 includes a handle assembly 102 connected to an elongate tissue access assembly 104. The elongate tissue access assembly 104 houses components employed to form an anchor assembly and is sized to fit into a 19 F cystosopic sheath for patient tolerance during a procedure in which the patient is awake rather than under general anesthesia. The tissue access assembly is stiff to allow manual compression of tissue at an interventional site by leveraging or pushing the handle assembly 102.

The anchor delivery device 100 further includes a number of subassemblies. A handle case assembly 106 including mating handle parts which form part of the handle assembly 102. The handle assembly 102 is sized and shaped to fit comfortably within an operator's hand and can be formed from conventional materials. Windows can be formed in the handle case assembly 106 to provide access to internal mechanisms of the device so that a manual override is available to the operator in the event the interventional procedure needs to be abandoned.

In one embodiment, the delivery device 100 is equipped with various activatable members which facilitate assembly and delivery of an anchor assembly at an interventional site. A needle actuator 108 is provided and as described in detail below, effectuates the advancement of one or more needle assemblies to an interventional site. In a preferred embodiment, the needle assembly has a needle that moves through a curved trajectory and exits the needle housing in alignment with a handle element, and in particular embodiments, in alignment with the grip. In various other embodiments, the needle housing is oriented such that the needles exit the housing at either the two o'clock or ten o'clock positions relative to a handle grip that is vertical. A needle retraction lever assembly 110 is also provided and when actuated causes the needle assembly to be withdrawn and expose the first anchor component. This action and the structure involved is also described in detail below. Finally, the delivery device 100 is equipped with a rear or proximal anchor actuator assembly 112.

In one particular, non-limiting use in treating a prostate, the elongate tissue access portion 104 of a delivery device is placed within a urethra (UT) leading to a urinary bladder (UB) of a patient. In one approach, the delivery device can be placed within an introducer sheath (not shown) previously positioned in the urethra or alternatively, the delivery device can be inserted directly within the urethra. When employing an introducer sheath, the sheath can be attached to a sheath mount assembly (described below). The patient is positioned in lithotomy. The elongate portion 104 is advanced within the patient until a leading end thereof reaches the prostate gland (PG). In a specific approach, the side(s) (i.e., lobe(s)) of the prostate to be treated is chosen while the device extends through the bladder and the device is turned accordingly. The distal end of the elongate portion can be used to depress the urethra into the prostate gland by compressing the inner prostate tissue. The inside of the prostate gland (i.e., adenoma) is spongy and compressible and the outer surface (i.e., capsule) of the prostate gland is firm. By the physician viewing with an endoscope, he/she can depress the urethra into the prostate gland compressing the adenoma and creating the desired opening through the urethra. To accomplish this, the physician rotates the tool. The physician then pivots the tool laterally about the pubic symphysis PB relative to the patient's midline.

Figure 8A:
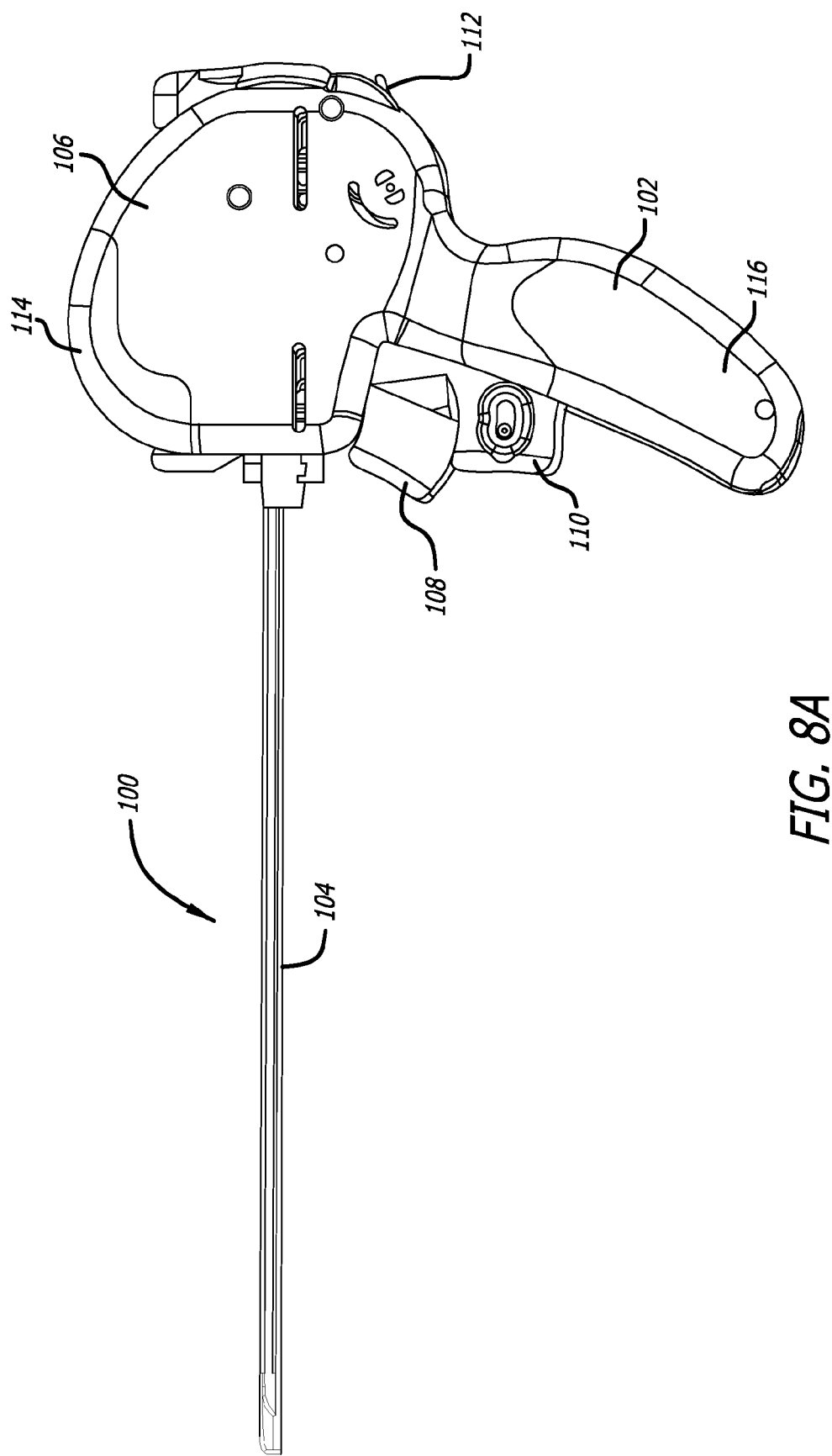
FIGS. 8A-D are side and perspective views, depicting one embodiment of a delivery device and various features thereof.
Figure 8B:
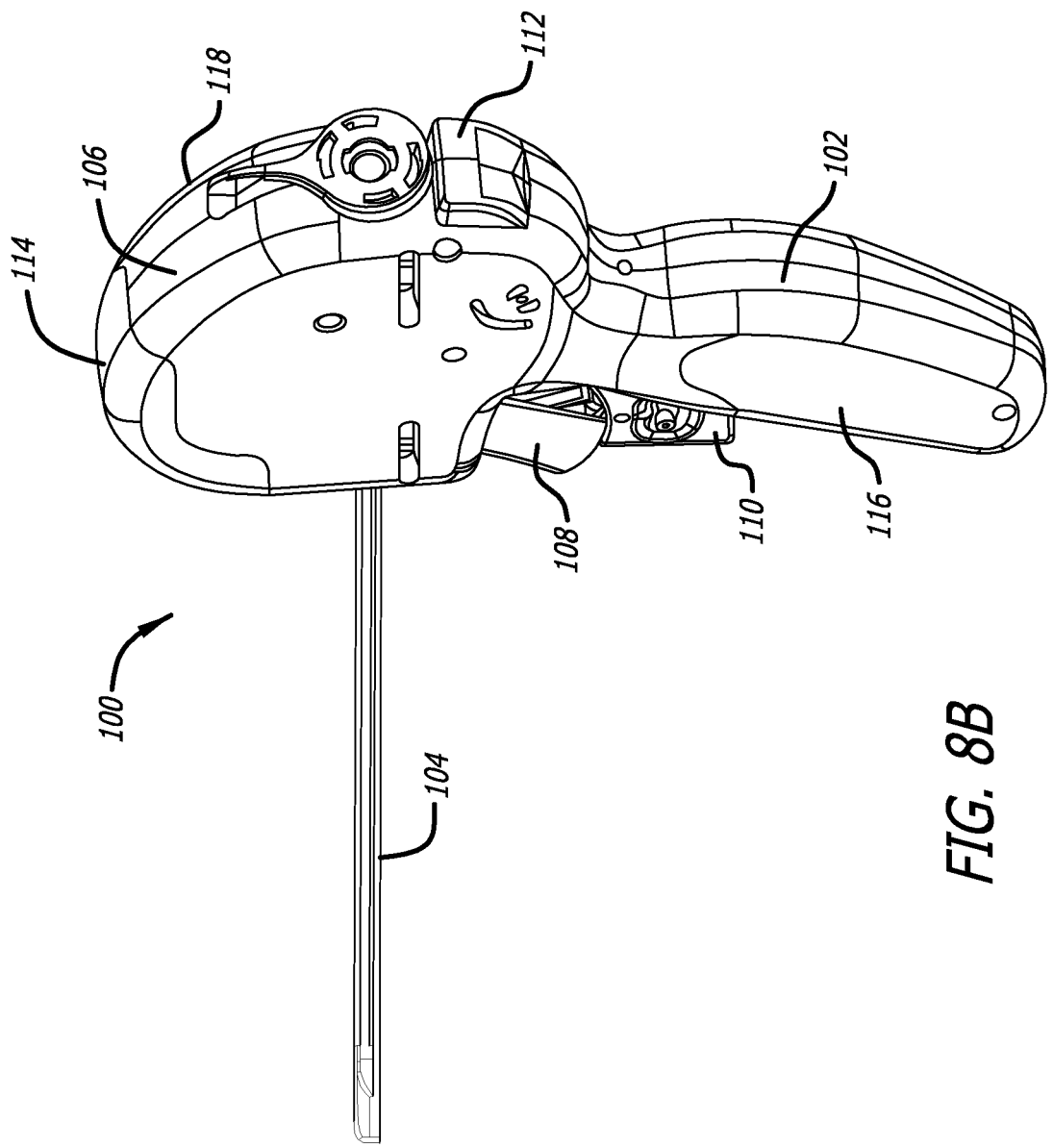

As shown in FIGS. 8A-B, the delivery device is at this stage configured in a ready state. The needle actuator 108 and the needle retracting lever 110 are in an inactivated position.

It is contemplated that the delivery device 100 includes two needles aligned side by side or over and under the delivery device to deliver the implant. The implant can include two capsular tabs attached to either end of a controlled length of suture or other connector. The connector can be woven to create a relatively larger diameter in the middle of the suture. When pressed against the side lobes of the prostate, the delivery device will compress the tissue sufficiently to allow the pre-determined length of the suture to keep the tissue in compression after release. The size of the prostate can be measured prior to the procedure so to allow a selection of the device with the proper suture length that will keep the tissue in compression. The suture could have a pledget inserted over the suture to provide a broader base for the tissue under pressure to prevent the suture from cutting into the soft tissue. In one approach, the suture can be a continuous length so that there is no requirement for a urethral end-piece or a cutting mechanism.

Figure 8C:
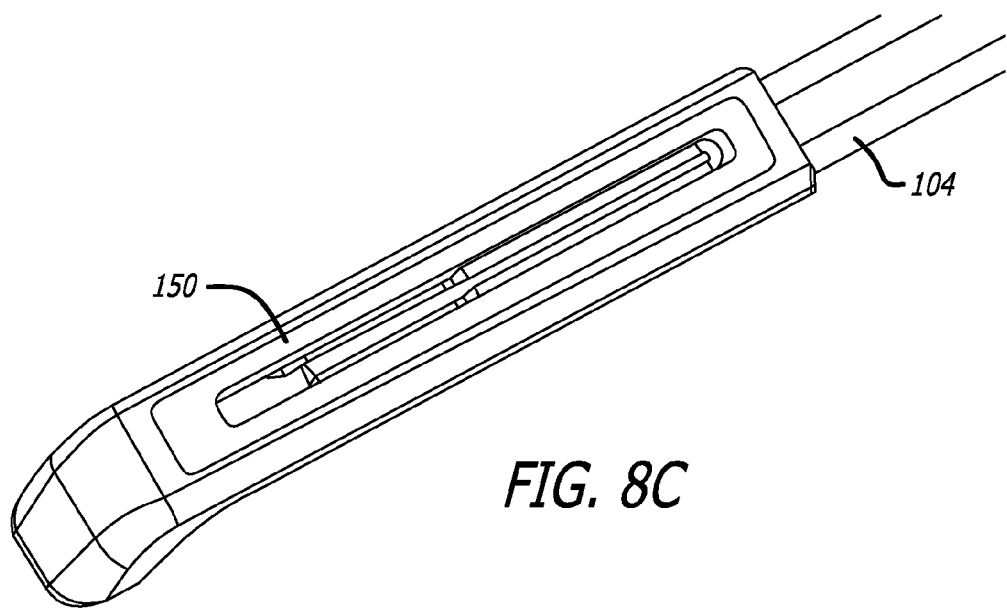
Figure 8D:
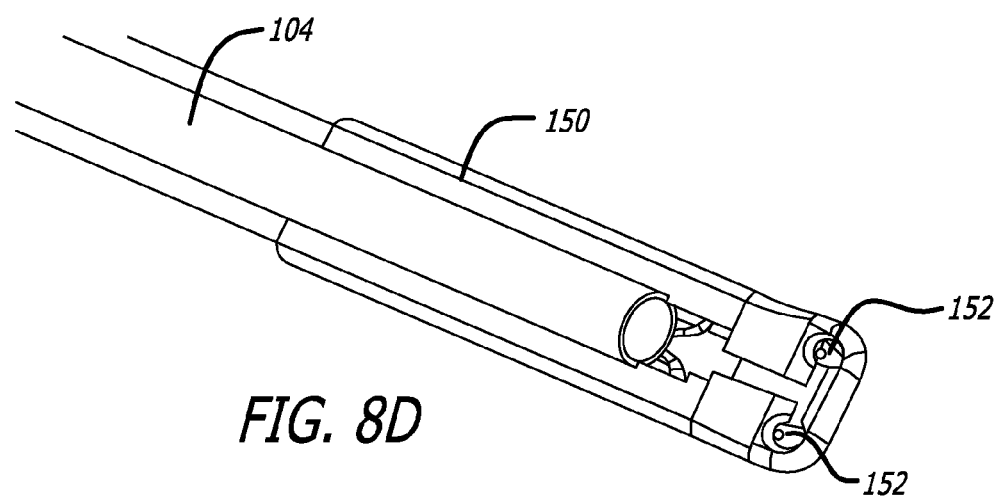

As shown in FIGS. 8C-D, a distal end of the delivery device 100 can be equipped with an end piece 150. The end piece 150 includes a pair of spaced channels 152, each being sized and shaped to accept a single needle assembly. Upon depression of the needle actuator 108, the needle assemblies are advanced from within the elongate member 104. The needle assemblies can be configured so that they curve back toward the handle as they are ejected. In use in a prostate intervention, the needle assemblies are advanced through and beyond a prostate gland (PG). Spring deployment helps to ensure that the needle passes swiftly through the tough outer capsule of the prostate without "tenting" the capsule or failing to pierce the capsule. In one approach, the needle is made from Nitinol tubing and can be coated with Parylene N. Such a coating helps compensate for frictional or environmental losses (i.e. wetness) which may degrade effectiveness of needle penetration.

After complete depression of the needle actuator 108 and the unlocking of the needle retraction lever 110, the needle retraction lever 110 can be actuated. Such action results in a withdrawal of the needle assemblies, leaving the connector of an anchor assembly in an extended position. In one embodiment, the needles are withdrawn further than its original position within the device pre-deployment. In a prostatic interventional procedure, this action can result in delivering first or distal anchor components attached to the connector beyond an outer surface of a prostate gland (PG) with the connector within a penetration tract in the prostate gland extending toward a terminal end of a delivery device.

Figure 9A:
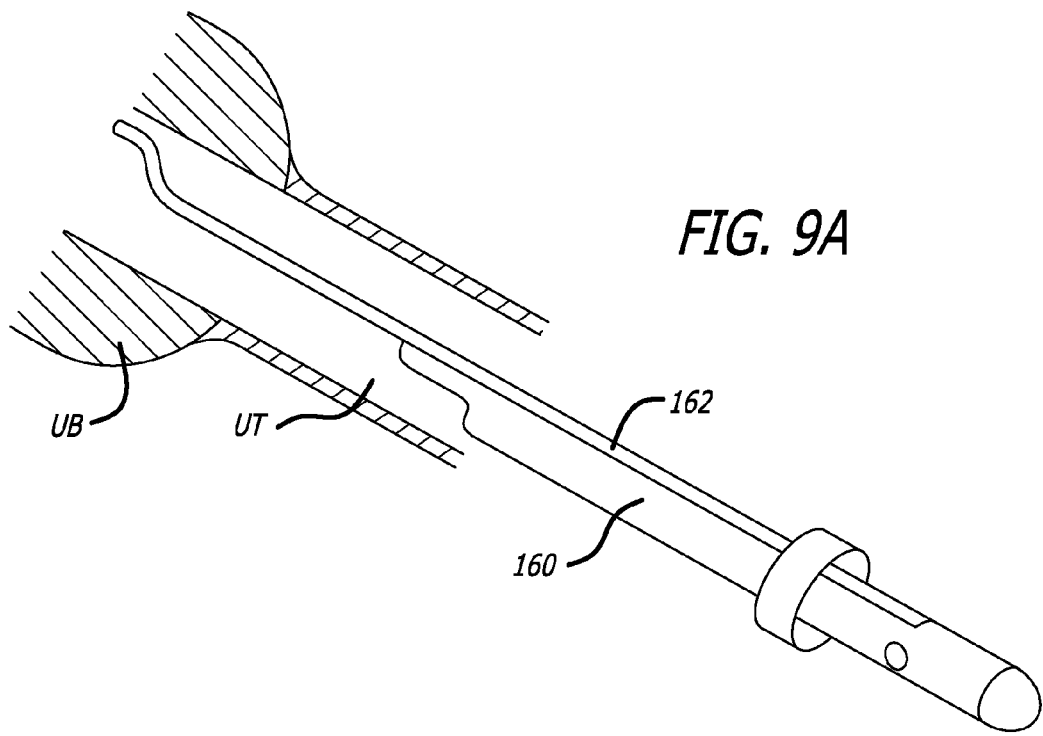
FIGS. 9A-C are perspective and side views, depicting an introducer sheath assembly and its interaction with a delivery device.

As stated, the delivery device can be placed within patient anatomy using an introducer sheath. During urology procedures that are performed in the urethra, irrigation that is required for good visibility of the operating field can lead to pain or short-term or long-term bladder damage. With reference to FIG. 9A, a cystoscopy sheath 160 (rigid or flexible) can be provided to alleviate this potential problem. The sheath 160 can be equipped with a separate lumen or drainage tube 162 that may be movable along a long axis of the sheath 160 or can otherwise be positioned with one end in the patient's bladder (UB) and one end outside the patient to allow for continuous or intermittent drainage during a procedure.

With this approach, a need to cross the bladder neck with the sheath 160 can be avoided. Moreover, pain and discomfort from a full bladder in a conscious patient is prevented as is bladder damage. Also, procedure time can be reduced by eliminating a separate drainage phase. Visibility also is improved via continuous flushing action as blood is removed more quickly from the interventional site and air bubbles are removed more quickly. It is further contemplated that fluid can be run in reverse to facilitate removal of air bubbles. A balloon or separate lumen could additionally secure the sheath 160. Proximal and distal position adjustment could be employed to eliminate a need to cross bladder neck and the separate lumen could be used to deliver drugs or analgesia.

Figure 9B:
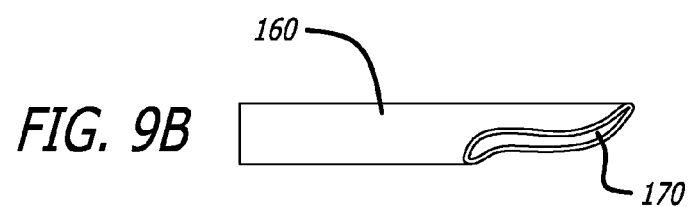
Figure 9C:
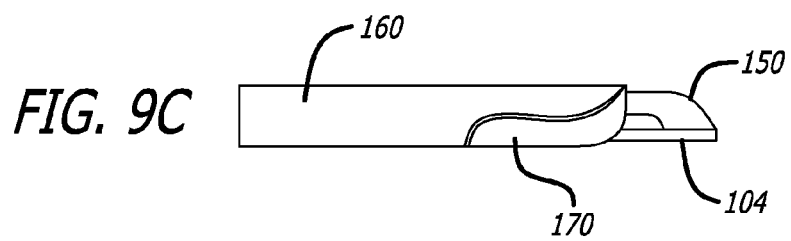

Turning now to FIGS. 9B-C, there is shown a tip assembly 170 that can be configured to be attached to an introducer sheath 160. In one approach, the tip assembly 170 is embodied in an overmold with a lip that snaps onto an edge of the sheath 160 and defines an atraumatic tip. The tip 170 eliminates any sharp edge which might come in contact with an implant in a prostatic urethra. The tip 170 can be an integral function of a sheath or can define a disposable tip that can be placed on a conventional sheath. Moreover, the tip 170 can be transparent so as to avoid being a visible obstruction.

Figure 10A:
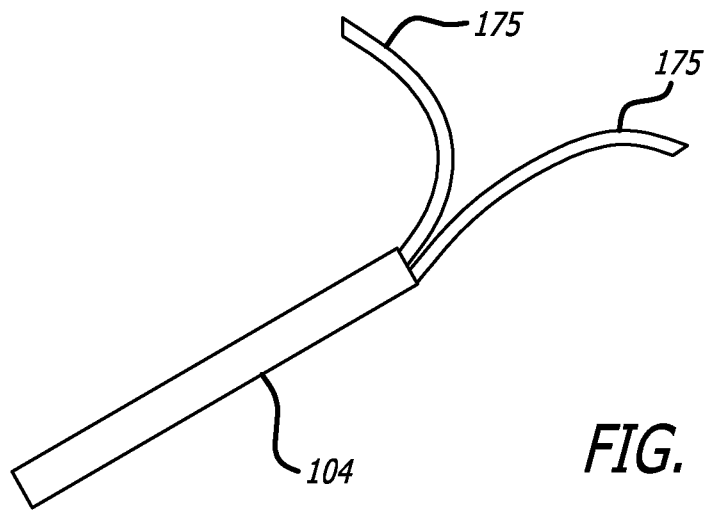
FIGS. 10A-B are perspective views, depicting various approaches to needle deployment.
Figure 10B:
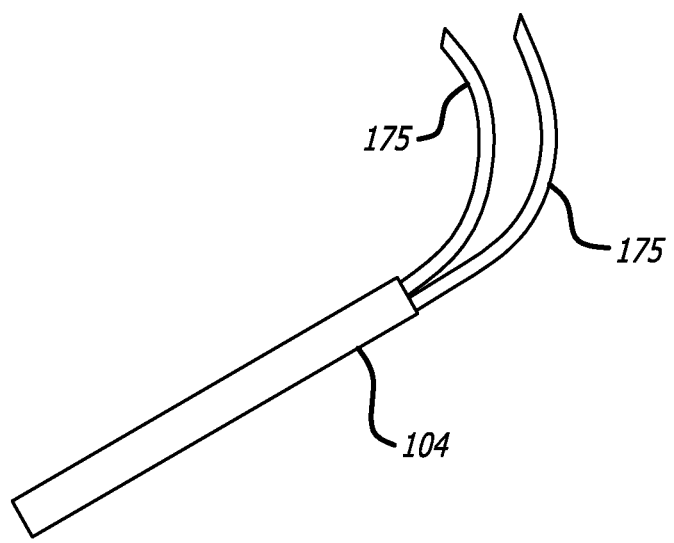

A dual needle deploy approach to creating a continuous channel or indentation in a prostate gland is contemplated (See FIGS. 10A-B). In this way, two urethral anchors or end pieces that are connected by suture, metal wire, or some other mechanism can be delivered to create a continuous indentation in the urethra. The relatively larger indentation created thus provides a greater area of deformity in the urethra, reshaping the prostate and allowing greater passage of urine through the larger continuous channel. As shown in FIGS. 10A-B, the delivery device 100 deploys two needles 175 at once. As such, the needles are able to treat the same side of the prostate with a defined spacing. As depicted in the figures, the needles 175 can be configured to provide a small or relatively large gap upon deployment. The delivery device 100 can also be adjusted to provide various desired gaps and angles of needle deployment. The needle 175 can also be extended to equal or varying lengths.

Figure 11A:
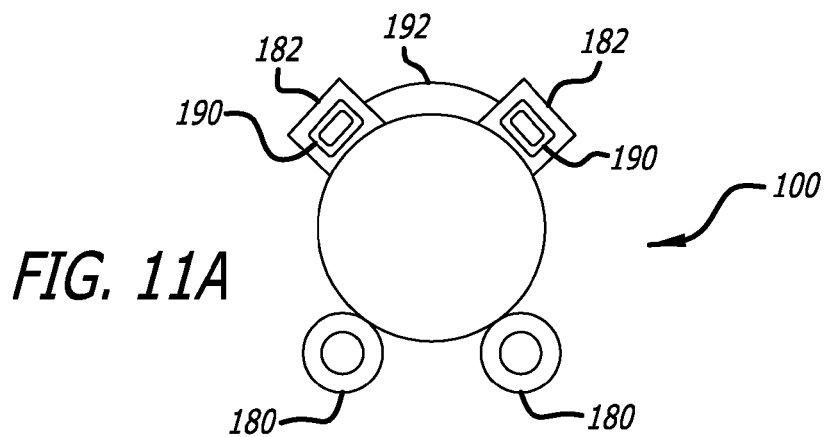
FIGS. 11A-E are cross-sectional views, depicting sub-assemblies of the delivery device.
Figure 11B:
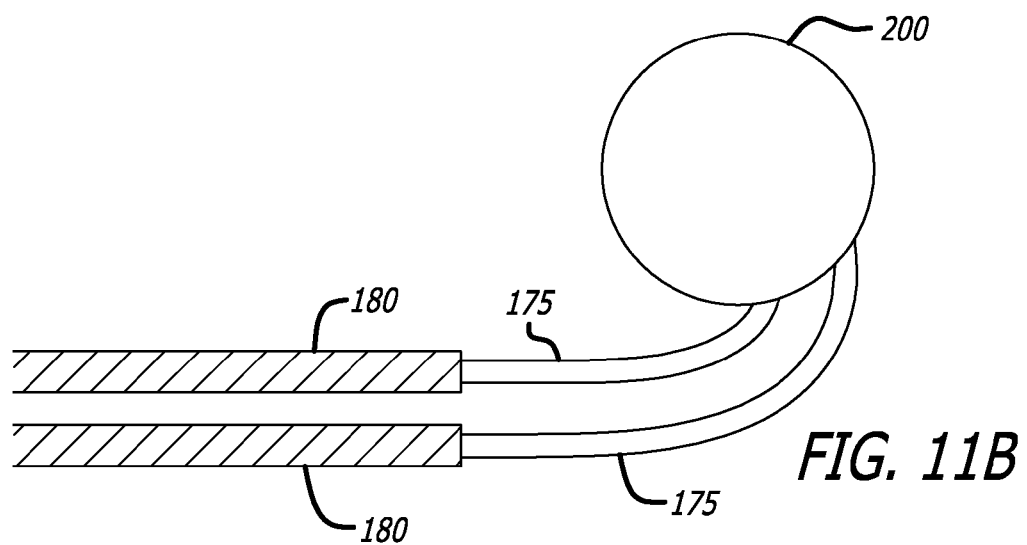

To accomplish a desired needle deployment, as shown in the cross-sectional view of FIG. 11A, the delivery device 100 can be equipped with a pair of spaced needle housings 180. The needle housings 180 are sized and shaped to each receive a single needle. The spacing of the housings 180 about a perimeter of a delivery device shaft can define the spacing and trajectory of the needles upon deployment. Thus, the housings can be arranged to project needles in parallel, divergent or crossing patterns. Attached to the delivery device shaft can also be a pair of spaced anchor housings 182. Contained within each anchor housing 182 is one urethral end piece or anchor 190. The two anchors or end pieces are connected by a wire, suture or elastic or inelastic connector 192.

Figure 11C:
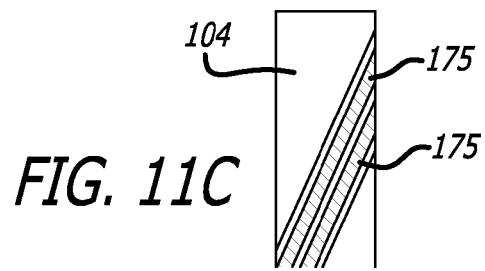
Figure 11D:
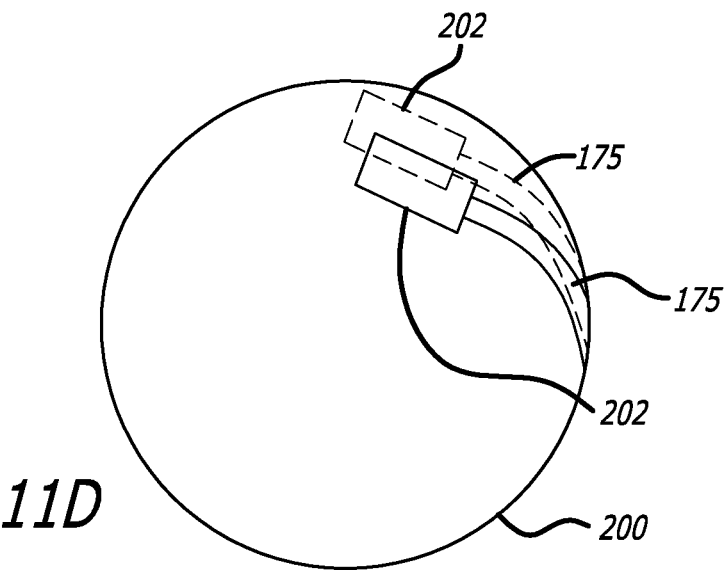

In this assembly approach, the needle would share a single spool 200. The two needles 175 could share the same track formed in the spool 200 or could reside in parallel tracks with a divider between the two. The lengths of each needle 175 may need to be adjusted to compensate for small differences in the track length so that the deployed needle lengths are the same. Efforts can likewise be taken so that the needle lengths are variable. At a distal end of the delivery device (FIG. 11C), a curved or other desirable exit route can be provided to properly guide the needles 175 into tissue. Further, as shown in FIG. 11D, needle overmolds 202 can be provided at proximal end portions of a needle 175 for attachment to the spool 200. Such overmolds 202 can be staggered and/or located on opposite sides of the needle spool 200.

Figure 11E:
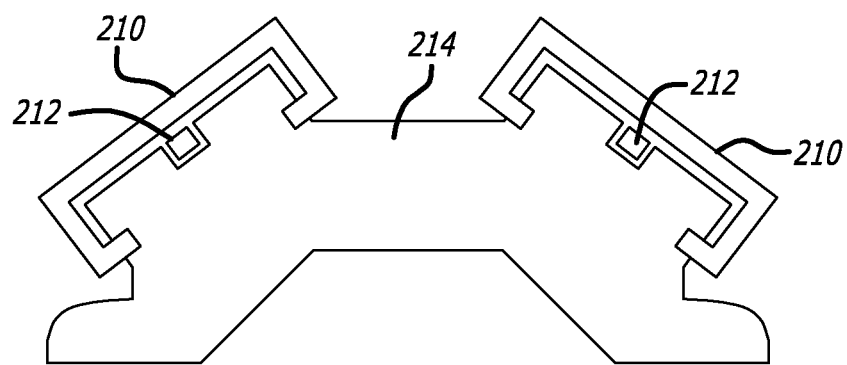

For the urethral side of the delivery mechanism (See FIG. 11E), the delivery device can include a pair of cutter block assemblies 210 and a pair of pusher assemblies 212 attached to a guide wing assembly 214. The cutter blocks 210 and pushers 212 can be individually molded components which are spaced upon the guide wing 214. At the appropriate moment, the pusher 212 advances urethral anchor components to the proper position. Subsequently, upon activation of the delivery device, the cutter blocks 210 are mobilized to cut the connector on a proximal side of a urethral anchor component.

Figure 12A:
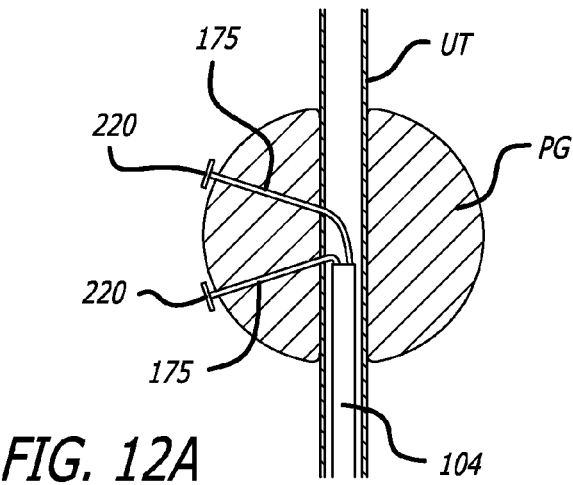
FIGS. 12A-C are partial cross-sectional views, depicting one implant delivery approach.
Figure 12B:
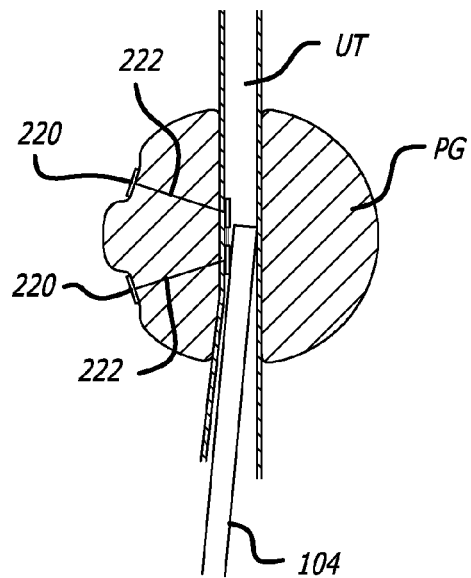
Figure 12C:
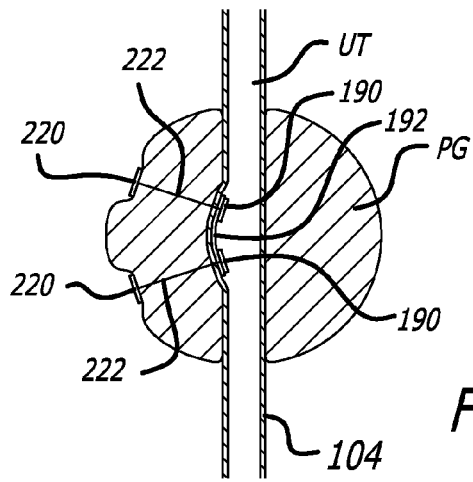

As best seen in FIGS. 12A-C, in a first step, the needles 175 are projected from the elongate shaft 104 of the delivery device 100 at desired angles from within the urethra (UT) and across the prostate (PG). In one approach, the needles 175 are extended beyond a prostate capsule. A distal anchor component 220 is then placed on an outside surface of a prostate (PG) or within the prostate (PG) or in apposition with other tissue (FIG. 12A). Next, the needles 175 are withdrawn exposing the connector 222 between the distal anchor components 220 and the proximal or urethral anchor components (FIG. 12B). Subsequently, the proximal components are ejected from the delivery device using the pushers and the connector 222 is cut to length by the cutter assemblies (FIG. 12C). The delivery device is then removed from the interventional area. The connector 192 joining the proximal anchors 190 creates a continuous indentation or channel in the prosthetic urethra (UT) between the two entry points adjacent the proximal anchor 190.

The formation of the continuous channel in this as well as the other disclosed approaches can be undertaken along with steps to shrink the prostate. Thus, in one or more embodiments, drug elution can be combined with urethral expanding. In this way, a specific urethral channel can be created acutely, then further enhanced by drug delivery along the channel to thereby make the acute effect more durable. To accomplish this, a needle is inserted within the prostate and prostate shrinking drugs such as pynasteride and dutasteride, or other adoptic and toxin drugs, can be injected to pass through relatively lower resistance pathways (tissue planes, fluid pathways) in the prostate. The result is that over time, the size of the prostate remains reduced and the channel created in the prostate is more durable.

Figure 13A:
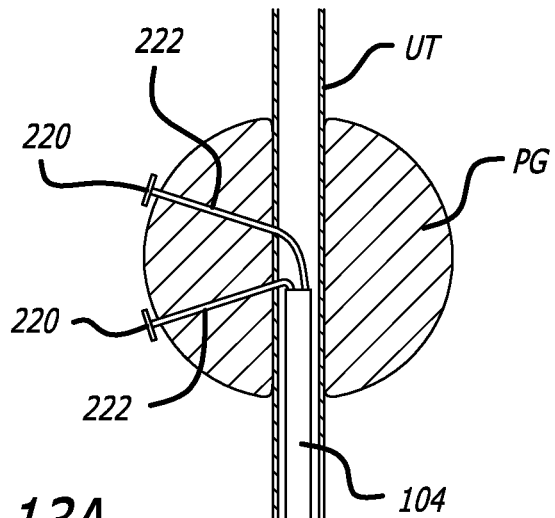
FIGS. 13A-B are partial cross-sectional views, depicting another approach to prostate treatment.
Figure 13B:
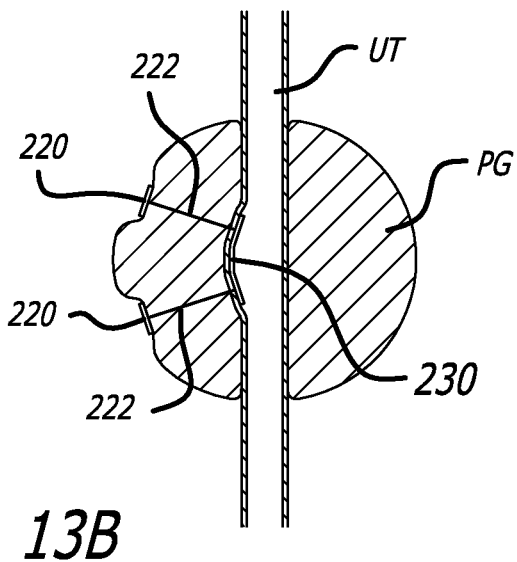

In a related approach, as shown in FIGS. 13A-B, the delivery device is employed to deliver distal anchor components in a body location displaced from the urethra (UT), such as against an exterior of a prostate (PL) capsule. However, rather than using a plurality of proximal anchor components attached by a connector, an elongate proximal anchor 230 attached by connectors 222 to the distal anchor components 220 is used to create a continuous indentation in a prostatic urethra (UT). In this way, a simplified mechanism can be incorporated within the delivery device to accomplish the ejection and deployment of a monolithic proximal anchor. The length of such an anchor can be selected to form the desired prostatic indentation.

Figure 14A:
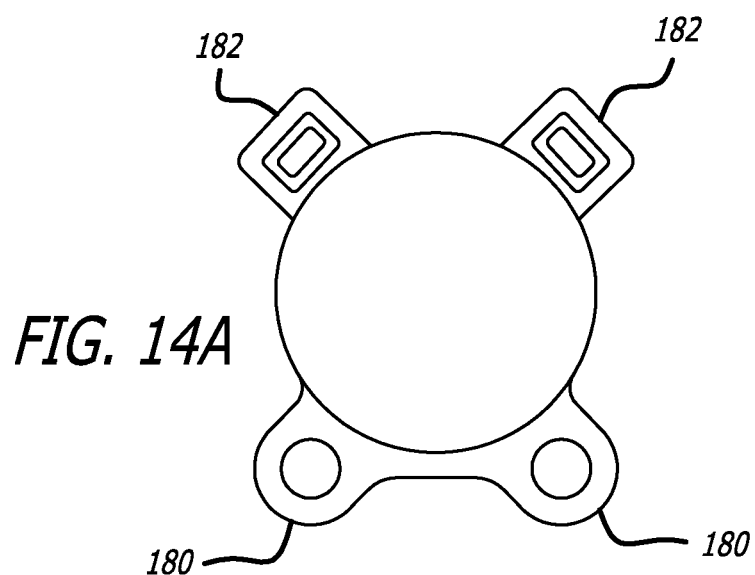
FIGS. 14A-B are partial cross-sectional views, depicting yet another prostate treatment approach.
Figure 14B:
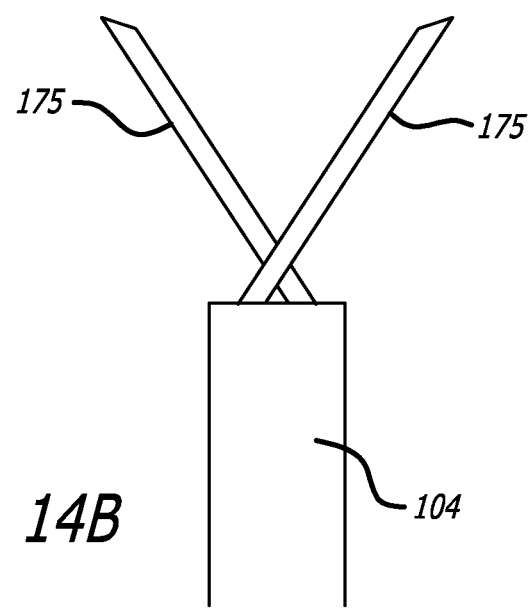

As shown in FIGS. 14A-B, a delivery device can alternatively be configured to embody lumens crossing in different planes. Thus, upon advancement of the needles 175, various crossing patterns for the anchor connectors can be achieved.

Figure 15A:
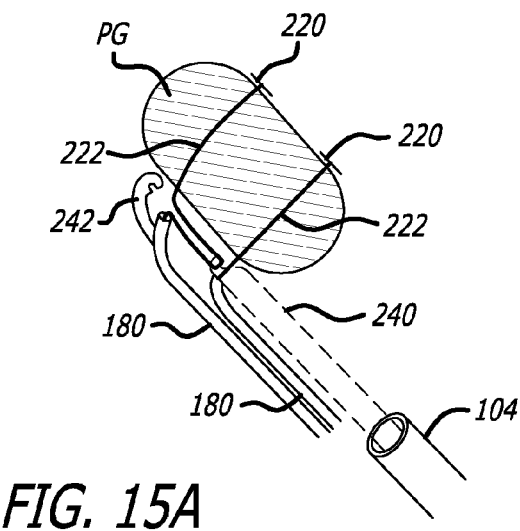
FIGS. 15A-B are partial cross-sectional views, depicting a still further prostate treatment approach.
Figure 15B:
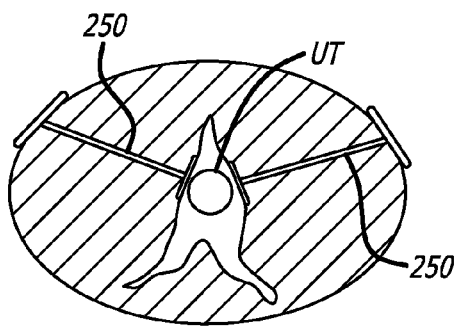

In another alternative approach, a two needle delivery device including a snare wire 240 that encircles both needle exit positions is provided to connect proximal anchors in situ (See FIGS. 15A-B). After needle and capsular anchor deployment, the snare wire 240 is retracted towards the delivery system thereby pulling both connectors 222 into a capture tube, such as the elongate member 104 of the delivery device. The capture tube can then be used to permanently or adjustably fix the two connectors 222 together. The fixation could be via a crimp, adhesive (e.g. cyanoacrylate or two part-epoxy), polymeric remelt, or knotting, among other methods. The amount of displacement of the snare wire 240 can be force-controlled or distance-controlled by the delivery device or controlled by the user in order to set an appropriate amount of tissue compression. One or both needle guides 180 could be adjustable in the axial direction or in rotation to facilitate different lengths of prostates or different final suture orientations within the urethra. A reloadable device (not shown) could be made in which new suture-tab assemblies are reloaded and the snare wire is reset, thereby permitting the delivery device to be reused within one patient. A reloadable device could be made in which new needles, suture-tab assemblies, and possibly snare wires are reloaded thereby permitting the delivery device to be reused within a patient or possibly between patients after steam or other means of sterilization. It is to be recognized that a device with only one needle could be used instead if the needle could contain and selectively deliver one capsular tab at a time and deliver two or more capsular tabs in a sequence for subsequent joining. The delivery device could also have more than two needles and deliver more than two capsular tabs for subsequent joining.

In use, the snare wire is secured in a snare wire holder 242 such that the needles 175 are routed inside the snare wire loop 240. After needle deployment, the snare wire 240 is pulled proximal thereby pulling the connector 222 towards and into the snare wire capture tube 140. Tension is at this time applied to the connectors. The snare wire capture tube 140 would contain adhesive or a crimp tip or ferrule (not shown) to permanently join the connectors. In one approach, the snare wire 204 itself could be the joining device a slip knot or snare wire could be advanced such that they are fixed relative to each other. Accordingly, the snare wire 244 or other connector attaching structure is thus positioned to form the continuous urethral indentations 250.

Figure 16A:
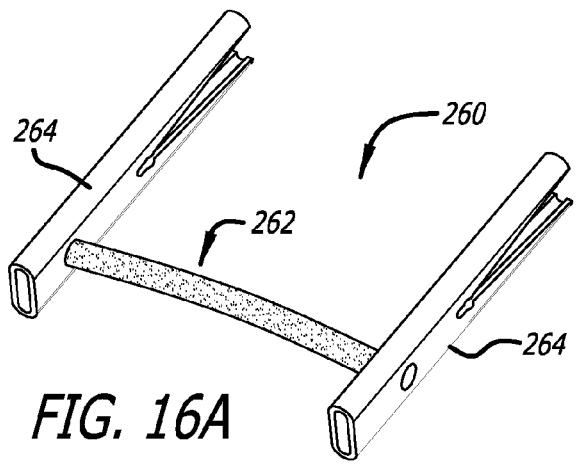
FIGS. 16A-B are perspective views, depicting alternative approaches to an anchor assembly.
Figure 16B:
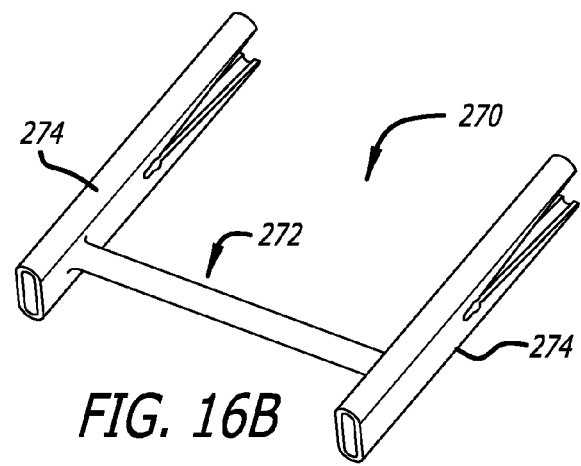

With reference now to FIGS. 16A-B, there is shown other alternative approaches to anchor assemblies for creating a continuous channel or indentations. In a first approach (FIG. 16A), an anchor assembly 260 can include an elastic member 262 connecting first and second generally elongate, split anchor members 264. The length of such anchor members can be selected for providing a secure footing as well as to create the desired channel in body tissue. In a second approach (FIG. 16B), the anchor 270 can be one continuous structure including a connector 272 made from metal, for example, which connects anchor members 274.

Figure 17A:
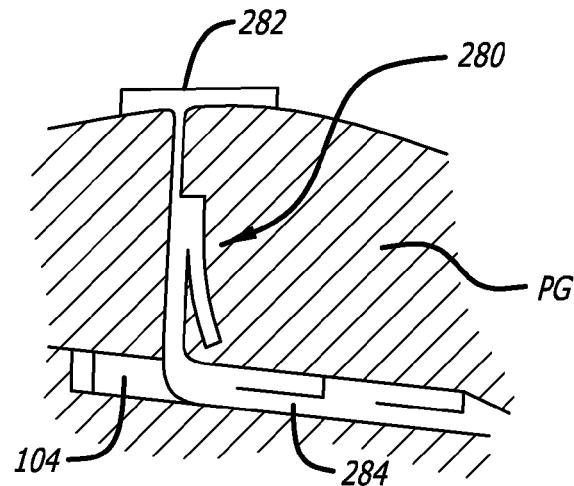
FIGS. 17A-C are perspective and partial cross-sectional views, depicting another approach to an anchor assembly.
Figure 17B:
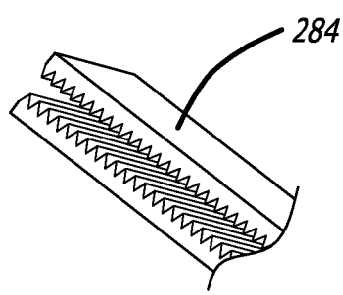
Figure 17C:
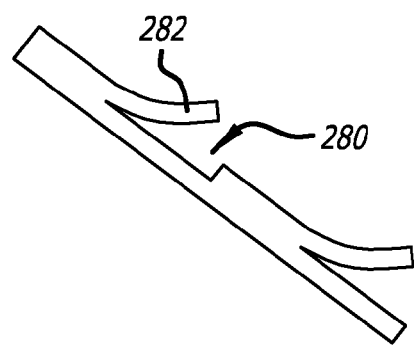

Various other approaches to structure for providing a continuous channel or indentation in prostatic urethral lobes are also contemplated. As shown in FIGS. 17A-C, an anchor assembly 280 embodying a repeating geometric capsular or distal anchor component 282 with a continuously locking urethral or proximal component 284 can be employed to create a desired indentation or channel. The repeating geometric structure enables a physician or other operator to use the anchor 280 in multiple applications where patient anatomy is varied. The locking structure of the proximal component allows for the proximal component to define a closed structure for use in creating the channel or indentation in the urethral prostate.

Figure 18A:
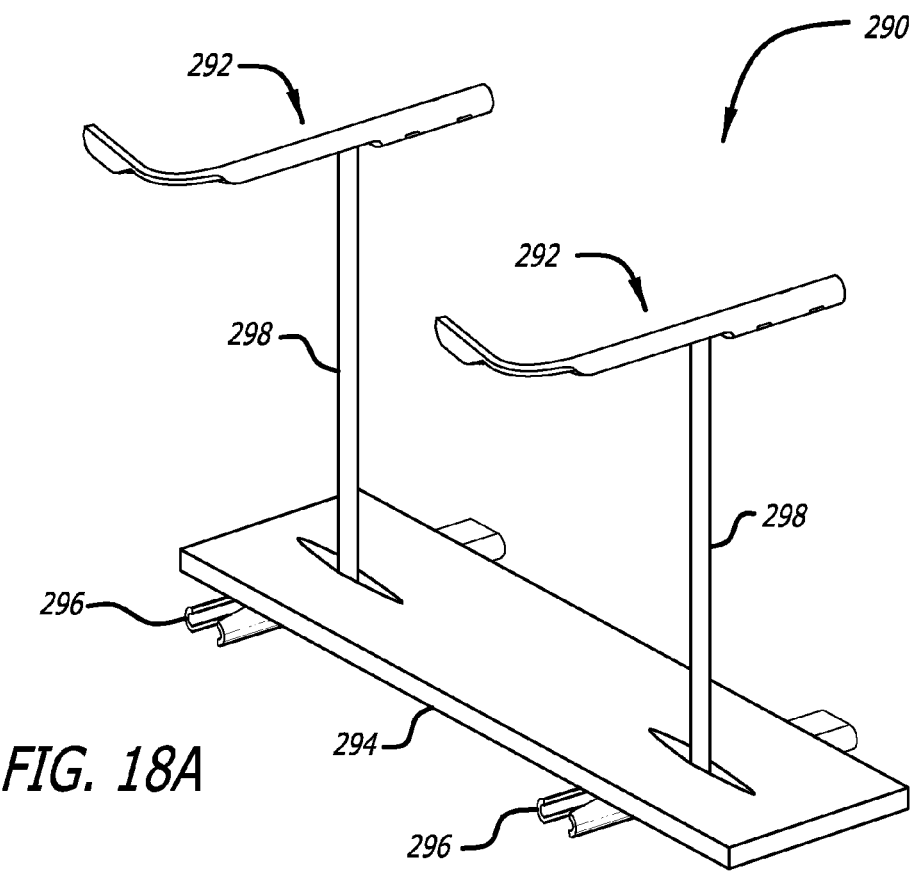
FIGS. 18A-B are perspective and partial cross-sectional views, depicting a further approach to an anchor assembly.
Figure 18B:
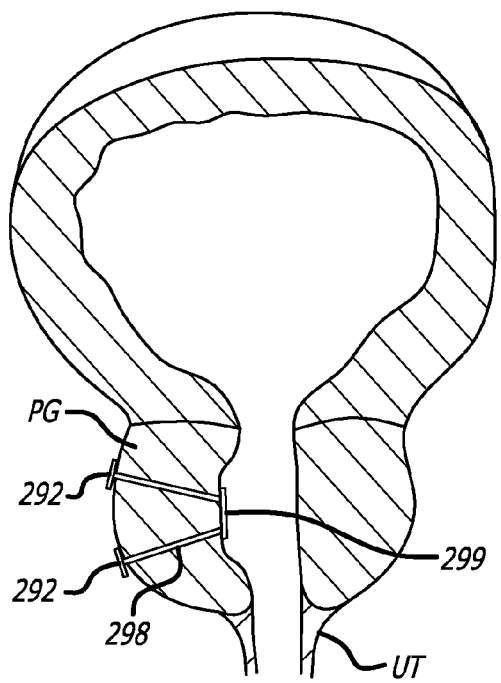

In another embodiment (FIGS. 18A-B), the anchor assembly 290 can embody a distal component 292 and a proximal component formed by a polymer or metal tape or bar 294 with holes or slits (at least two) along its length. A delivery instrument positions the bar/tape against the prostate lobe and delivers an anchor system 290 or equivalent through each slit or hole in the bar/tape. The delivery system would contain at least one needle each housing at least one distal anchor 292 attached to a length of suture 298. It would also contain at least two proximal anchors 296 that lock the bar/tape 294 to the suture 298. One variation is to add barbs or bumps (not shown) to the suture 298 that would allow for adjustment and in the bar position and anchoring of the bar without the use of a proximal anchor 296. Another variation is to have a single suture connect to a long leaf spring (not shown) in the urethra which is formed by insertion of a balloon or by a mechanical feature in the delivery instrument. Yet another variation would involve a single proximal anchor connected to two distal anchors.

Figure 19A:
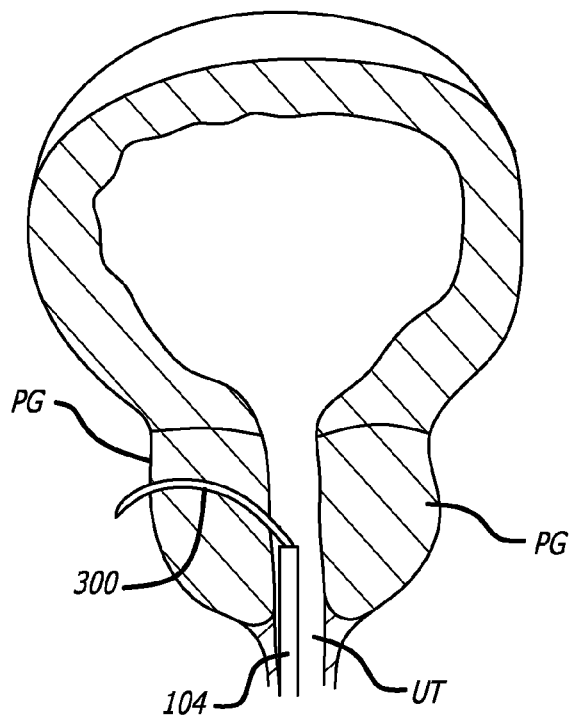
FIGS. 19A-B are partial cross-sectional views, depicting a yet further approach to an anchor assembly.
Figure 19B:
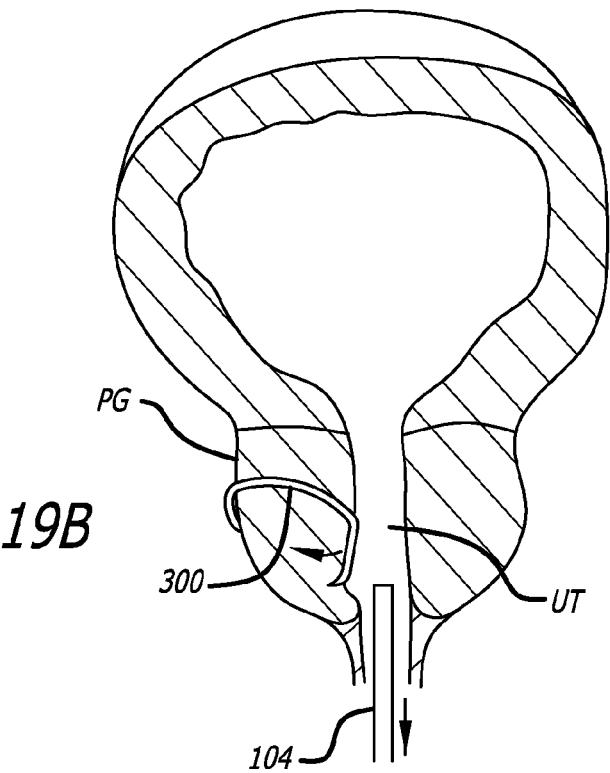
Figure 20A:
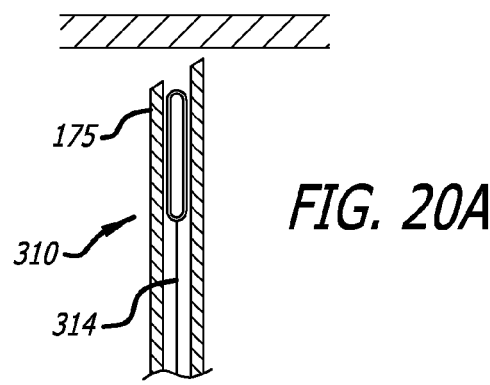
FIGS. 20A-C are partial cross-sectional views, depicting an alternative distal anchor component.
Figure 20B:
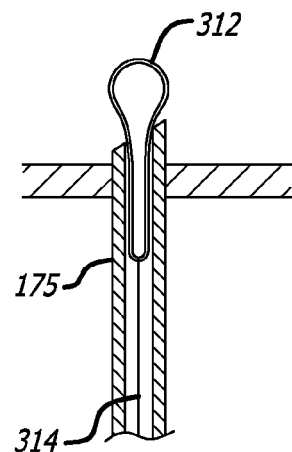
Figure 20C:
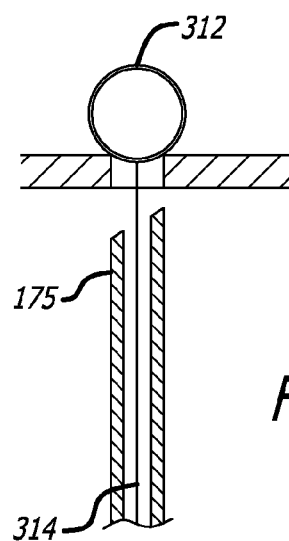
Figure 21A:
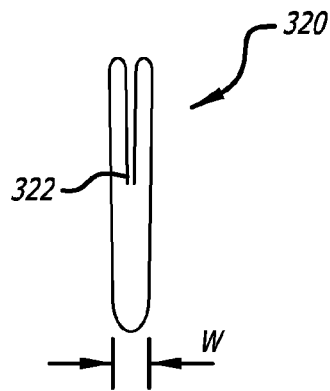
FIGS. 21A-D are side views, depicting various other alternative approaches to anchor end components.
Figure 21B:
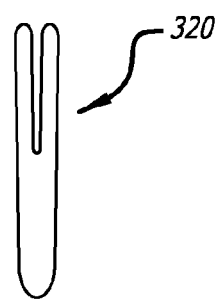
Figure 21C:
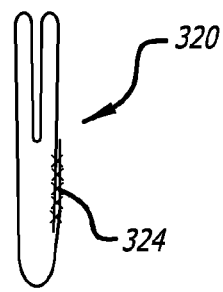
Figure 21D:
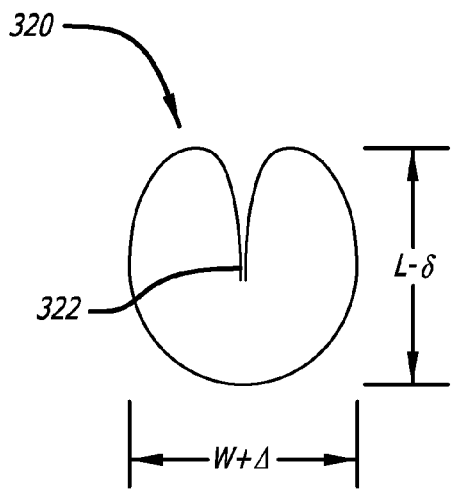

A further approach to structure for creating a continuous channel is shown in FIGS. 19A-B. Here, the defect or channel forming structure is embodied in a stainless steel, polymer, or Nitinol needle or curved wire 300 that acts as a single-piece implanted tissue anchor. The anchor is delivered first through the urethral wall (UT), then through the capsular wall of the prostate (PG). The anchor 300 bends back on itself as its feeds out of distal portion of a delivery device 104, until it is released completely from the device. It may be a shape-memory material or it may be formed as it is fed out of the delivery device (e.g. SS curls onto itself as it is cold worked). This bending causes the distal end of the needle or wire to hook into the capsular layer of the prostate (PG), and the proximal end(s) to curl onto itself as it is released, pulling the urethral (UT) side of the prostate towards the capsule or outer peripheral of the prostate gland (PG). It is contemplated that the implant 300 takes shape when deployed by a delivery instrument due to pre-set shape (Nitinol) or due to interaction with delivery device upon release. In a variation on this approach, the wire or needle 300 has multiple proximal ends for engaging a proximal side of the prostate gland.

Turning now to FIGS. 20A-24C, further approaches to anchor assemblies are presented. In a first alternative approach, an anchor assembly 310 including a single circular loop 312 made from a flexible material can define a distal component. A suture 314 is attached to one end of the loop. The anchor is delivered through a minimally invasive small diameter cannula or needle 175. This type of anchor has the ability to fit within a small cannula or needle due to its flexible nature. Once the anchor is pushed out from the cannula/needle 175, the loop 312 springs back to its original circular loop shape. Since the diameter of this anchor is significantly larger than the hole created by the cannula/needle, the anchor cannot slip back into the hole that it was introduced through. One benefit of this design is the simplicity of the anchor itself. The loop is a one piece design with no articulating joints. As tension is applied to the suture the geometric shape of the anchor is self centering and would anchor in any orientation. It is contemplated that the anchor can be made from a variety of flexible materials ranging from Nitinol, polymers, titanium or stainless steel.

As shown in FIGS. 21A-D, an anchor 320 can embody other structure requiring a small delivery geometry to permit minimally invasive insertion and a large in situ geometry to help engage tissue for maximum holding force. In this particular embodiment, a tissue anchor defining a hoop that expands in width as it contracts in length is contemplated. The width expansion is relatively large compared to the length contraction (See FIG. 21D). The device can be a wire form made from a shape memory or other metal or it could be a molded polymer with sufficient elasticity to survive the shape transformation. It could be encased in a membrane, a polymeric sack, or encapsulated in an elastomer to provide biocompatibility, tissue ingrowth, drug delivery, or mechanical stability features. Additionally, the wire form can define a continuous structure (FIG. 21B) or can define a loop with a pair of unconnected terminal ends 322. In one approach, a weld or adhesive 324 can be employed to join ends of the wire to create a closed structure.

Figure 22A:
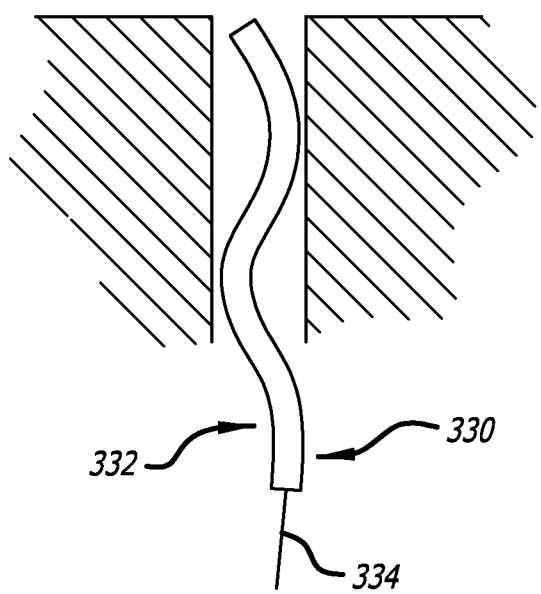
FIGS. 22A-B are partial cross-sectional views, depicting further alternative approaches to distal anchor components.
Figure 22B:
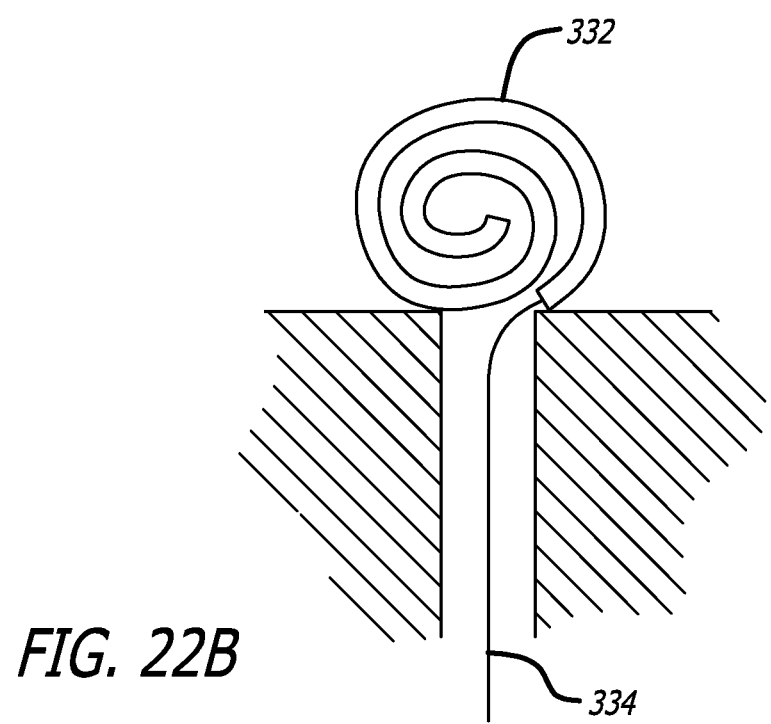

With reference to FIGS. 22A-B, the anchor assembly 330 can also include a tissue anchor 332 having a pre-set coiled shape. The coiled tissue anchor 332 is attached at its proximal end to a suture or other connector structure 334. During delivery, the coiled portion assumes an elongated configuration. Upon release at the interventional site, the coiled anchor returns to its pre-set shape to provide the desired tissue engaging function.

Figure 23A:
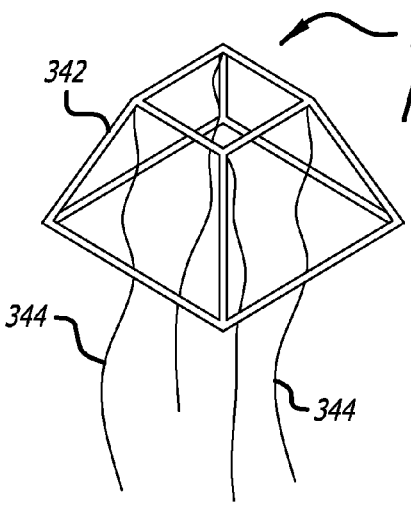
FIGS. 23A-B are perspective views, depicting an umbrella anchor component.
Figure 23B:
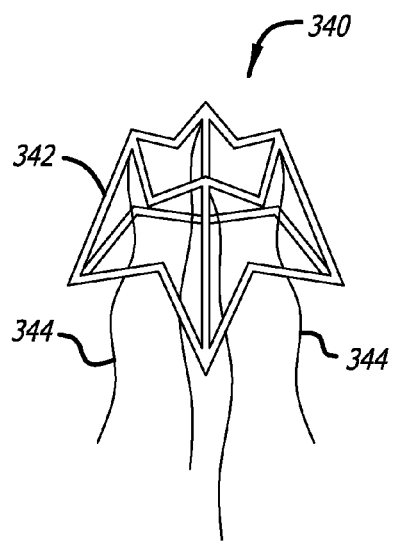
Figure 24A:
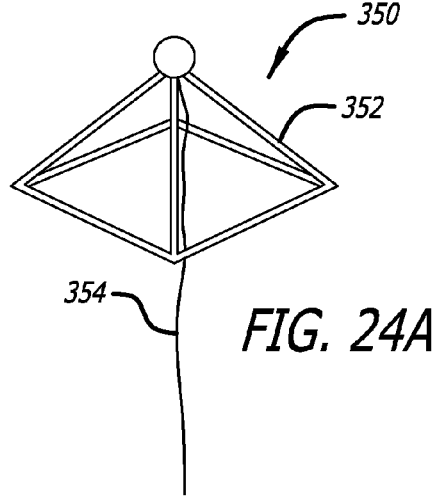
FIGS. 24A-C are perspective views, depicting alternative umbrella anchor components.
Figure 24B:
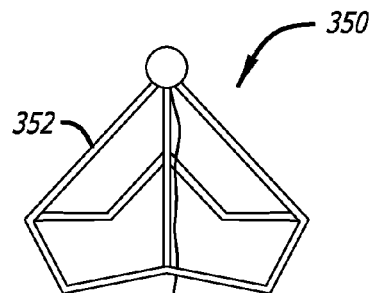
Figure 24C:
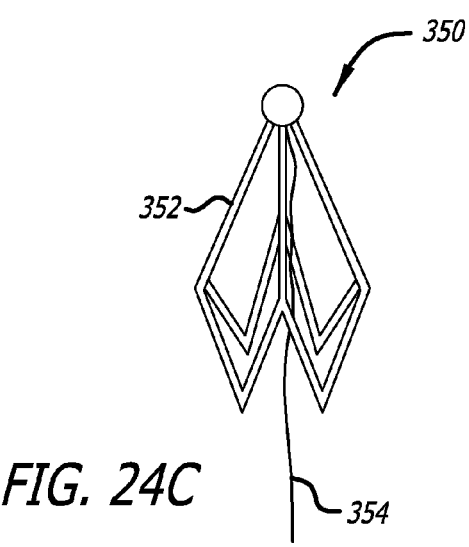
Figure 25A:
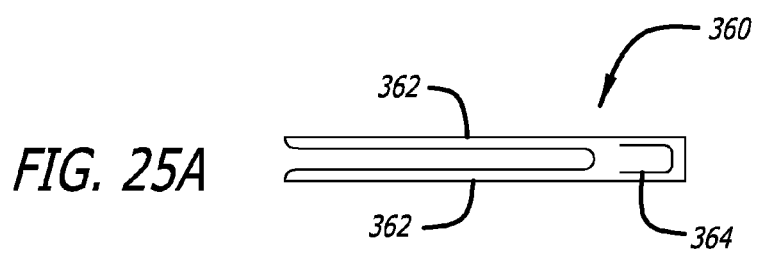
FIGS. 25A-D are side and perspective views, depicting further alternative approaches to anchor components.
Figure 25B:
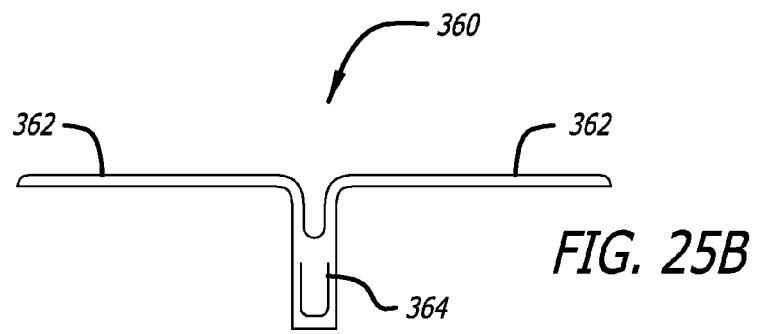
Figure 25C:
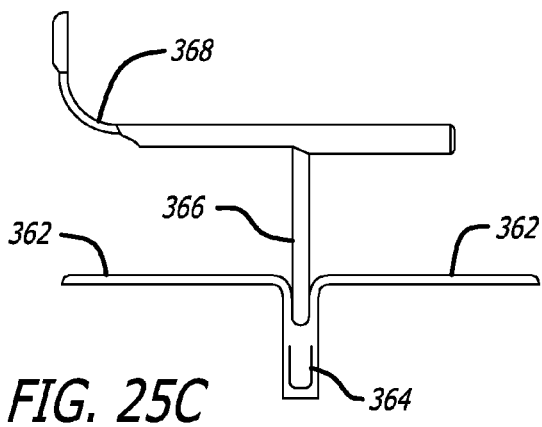
Figure 25D:
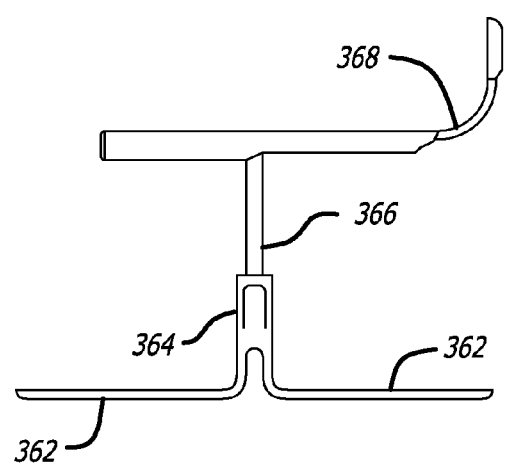
Figure 26A:
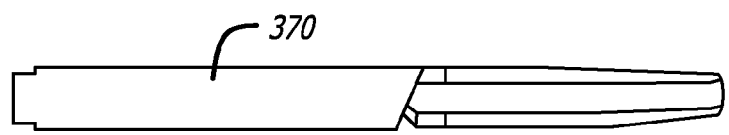
FIGS. 26A-D are side and perspective views, depicting yet further anchor components.
Figure 26B:
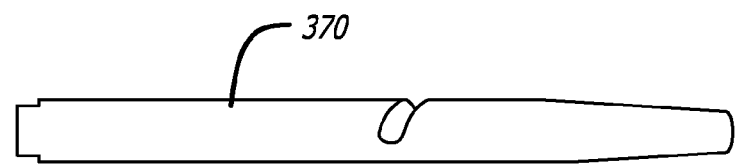
Figure 26C:
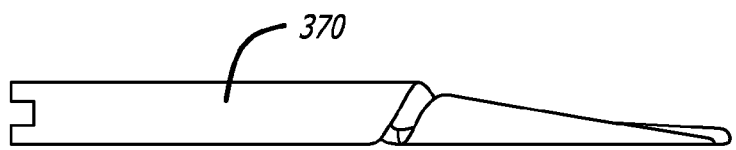
Figure 26D:
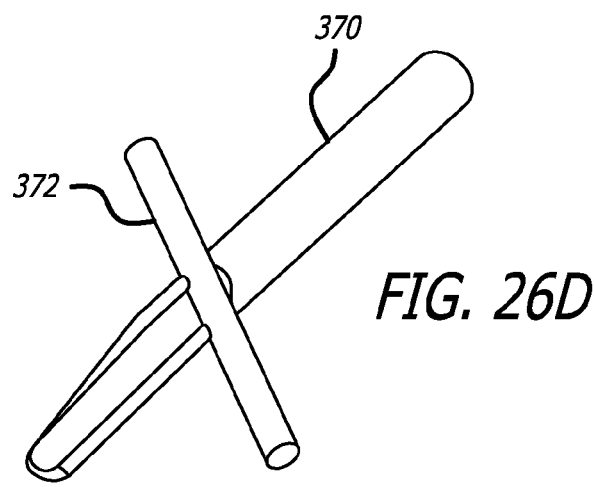

Various approaches to umbrella-like anchor structures are shown in FIGS. 23A-B and 24A-C. As shown in FIGS. 23A-B, the anchor assembly 340 includes an expandable frame 342 connected to a plurality of connecting members or sutures 344. Alternatively, an anchor assembly 350 including an umbrella frame 352 can be attached to a single suture 354. Thus, the tissue anchoring system 340 can consist of three or more lengths of suture 344 and a metal or plastic anchor 342 with stiff linkages connected by flexible joints which allow it to take on a folded state and an unfolded state. The system may also consist of a secondary anchor or multiple secondary anchors that are attached to the opposite end(s) of the suture(s) after the primary anchor has been delivered. In one contemplated approach, the umbrella anchor 340 may be delivered on the outside of a trocar, which facilitates a smaller delivery system, since the trocar can be of a relatively smaller diameter. Multiple sutures 344 attached to a single primary anchor provide a strong system which can withstand higher loads if the sutures are bundled together and attached to a single secondary anchor. Alternatively, if the sutures are each attached to an individual secondary anchor, the system can treat multiple tissue areas with a single primary anchor. The umbrella anchor is intended to cover a large area of tissue. This results in the creation of a larger defect on the primary tissue plane. In the alternative approach, the folding anchor 350 attached to a single length 354 of suture can be delivered from within a needle, but otherwise functions the same.

As shown in FIGS. 25A-D, a proximal anchor component can also define a dual strut anchor 360 including a pair of anchor prongs 362 extending from a body 364, the prongs 362 providing long-length tissue compression. The body 364 can further be attached to one end of a connector 366, the opposite end of which is secured to a distal anchor component 368 could be fabricated from stainless steel or Nitinol. In a pre-deployment condition, both anchor prongs 362 are held together in the delivery device and then the prongs 362 would unfold to provide long-length tissue compression upon implantation.

With reference to FIGS. 26A-D, the proximal anchor can also be defined by an anchor housing a cork-screw body 370. The corkscrew anchor provides a means to screw the anchor onto a connector 372. This concept could be used to deploy the anchor straight out from the distal end of a delivery device.

Figure 27A:
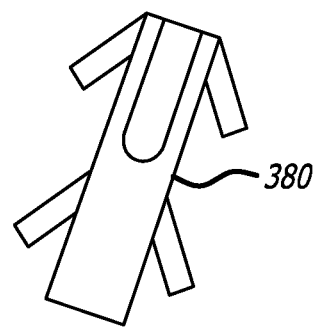
FIGS. 27A-C are perspective and side views, depicting other anchor components.
Figure 27B:
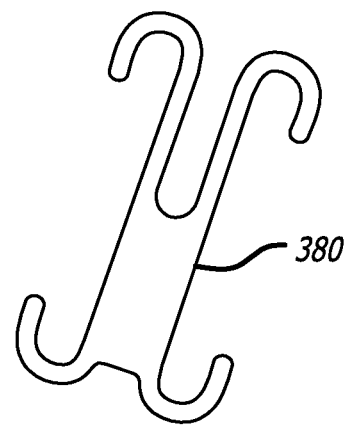
Figure 27C:
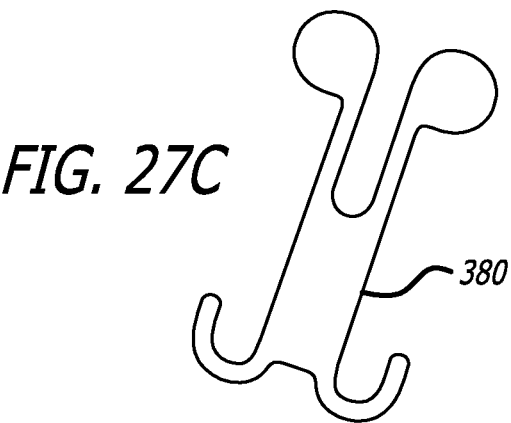

Finally, as shown in FIGS. 27A-C, anchor structure 380 can be formed or drawn tubing that is cut for suture or connector capture features. Numerous alternative geometries for the anchor exist, where the anchor 380 was a solid sheet that was laser cut. In addition, the anchor could be multiple parts that are assembled and puzzle pieced together after suture capture to form a larger area for tissue approximation.

Within a patient's body, the disclosed anchor assemblies are configured across anatomy within the interventional site. A continuous channel or indentation is formed in the prostate or prostatic urethra due to the anchor assembly compressing the surrounding enlarged prostate tissue due to the fact that the outer capsular tissue is rather strong, substantially non-compressible and non-displaceable while the adenoma of the prostate gland is compressible and the urethral wall displaceable.

During the procedure, as stated, a second catheter (not shown) with a vision system may be advanced into the urinary bladder UB to allow verification of anchor placement and tensioning from within the urinary bladder UB. The catheter or device may be flexible, rigid or semi-rigid. The needle may exit at the tip of the device, or may exit at the side of the device. Some portion or the entire catheter or device may have articulation control to allow for navigating and positioning.

Accordingly, the present invention contemplates both pushing directly on anchor portions of an anchor assembly as well as pushing directly upon the connector of the anchor assembly. Moreover, as presented above, the distal or first anchor component is advanced and deployed through one or more needle assemblies and at least one component of the proximal or second anchor component is advanced and deployed from a housing portion of the anchor deployment device. Further, either a single anchor assembly or multiple anchor assemblies can be delivered and deployed at an intervention site by the deployment device. Additionally, a single anchor assembly component can for example, be placed on one side of a prostate or urethra while multiple anchor assembly components can be positioned along an opposite or displaced position of such anatomy. The number and locations of the anchor assemblies can thus be equal and/or symmetrical, different in number and asymmetrical, or simply asymmetrically placed. In the context of prostate treatment, the present invention is used for the compression of the prostate gland and the opening of the prostatic urethra, the delivering of an implant at the interventional site, and applying tension between ends of the implant. Moreover, drug delivery is both contemplated and described as a further remedy in BPH and over active bladder treatment as well as treating prostate cancer and prostatitis.

Once implanted, the anchor assembly of the present invention accomplishes desired defect formation, tissue manipulation, approximation, compression or retraction as well as cooperates with the target anatomy to provide an atraumatic support structure. In one preferred embodiment, the shape and contour of the anchor assembly is configured so that the assembly invaginates within target tissue, such as within natural folds formed in the urethra by the opening of the urethra lumen by the anchor assembly. In fact, in situations where the anchor assembly is properly placed, wispy or pillowy tissue in the area collapses around the anchor structure. Eventually, the natural tissue can grow over the anchor assembly and new cell growth occurs over time. Such cooperation with target tissue facilitates healing and avoids unwanted side effects such as calcification or infection at the interventional site.

Subsequent to the interventional procedure, the patient can be directed to take alpha blockers for 2-4 weeks. Anti-inflammatory medicine can also be taken.

Furthermore, in addition to an intention to cooperate with natural tissue anatomy, the present invention also contemplates approaches to accelerate healing or induce scarring. Manners in which healing can be promoted can include employing abrasive materials, textured connectors, biologics and drugs.

Additionally, it is contemplated that the components of the anchor assembly or selected portions thereof (of any of the anchor assemblies described or contemplated), can be coated or embedded with therapeutic or diagnostic substances (e.g. drugs or therapeutic agents). Again, in the context of treating a prostate gland, the anchor assembly can be coated or imbedded with substances such as 5-alpha-reductase which cause the prostate to decrease in size. Other substances contemplated include but are not limited to phytochemicals generally, alpha-1a-adrenergic receptor blocking agents, smooth muscle relaxants, and agents that inhibit the conversion of testosterone to dihydrotestosterone. In one particular approach, the connector can for example, be coated with a polymer matrix or gel coating which retains the therapeutic or diagnostic substance and facilitates accomplishing the timed release thereof. Additionally, it is contemplated that bacteriostatic coatings as well as analgesics and antibiotics for prostatitis and other chemical coatings for cancer treatment, can be applied to various portions of the anchor assemblies described herein. Such coatings can have various thicknesses or a specific thickness such that it along with the connector itself matches the profile of a cylindrical portion of an anchor member affixed to the connector. Moreover, the co-delivery of a therapeutic or diagnostic gel or other substances through the implant deployment device or another medical device (i.e. catheter), and moreover an anchor assembly including the same, is within the scope of the present invention as is radio-loading devices (such as a capsular or distal ends of implants for cancer or other treatment modalities). In one such approach, the deployment device includes a reservoir holding the gel substance and through which an anchor device can be advance to pick up a desired quantity of therapeutic or diagnostic gel substance.

It is to be recognized that the timing of the dual advancement of the needles and connector assemblies and subsequent relative motion between the assemblies is coordinated. That is, the needle assembly or assemblies first provide access to an interventional site and then the connector assembly is left extending beyond a terminal end of the needle assembly through the relative motion of the needle and connector assemblies.

It is further contemplated that in certain embodiments, the anchor delivery device can include the ability to detect forces being applied thereby or other environmental conditions. Various sections of the device can include such devices and in one contemplated approach sensors can be placed along the needle assembly. In this way, an operator can detect for example, whether the needle has breached the target anatomical structure at the interventional site and the extent to which such breaching has occurred. Other sensors which can detect particular environmental features can also be employed such as blood or other chemical or constituent sensors. Moreover, one or more pressure sensors or sensors providing feedback on the state of deployment of the anchor assembly during delivery or after implantation are contemplated. For example, tension or depth feedback can be monitored by these sensors. Further, such sensors can be incorporated into the anchor assembly itself, other structure of the deployment device or in the anatomy.

Moreover, it is to be recognized that the foregoing procedure is reversible. In one approach, the connection of an anchor assembly can be severed and a proximal (or second) anchor component removed from the patient's body. For example, the physician can cut the connector and simultaneously remove the second anchor previously implanted for example, in the patient's urethra using electrosurgical, surgical or laser surgical devices used in performing transurethral prostate resection.

An aspect that the various embodiments of the present invention provide is the ability to deliver an anchor assembly having a customizable length, each anchor assembly being implanted at a different location without having to remove the device from the patient. Other aspects of the various embodiments of the present invention are load-based delivery, of an anchor assembly, anchor assembly delivery with a device having integrated connector, (e.g. suture), cutting, and anchor assembly delivery with an endoscope in the device. The delivery device is uniquely configured to hold the suture with tension during delivery to help ensure that the first anchor component sits firmly against a tissue plane (e.g., the outer capsule of the prostate) and is held relatively firm as the second anchor component is attached to the connector and the delivery device. In this aspect, the needle assembly acting as a penetrating member is cooperatively connected to a mechanism which pulls on the anchor while the needle assembly is retracted.

It is to be recognized that various materials are within the scope of the present invention for manufacturing the disclosed devices. Moreover, one or more components such as distal anchor, proximal anchor, and connector, of the one or more anchor devices disclosed herein can be completely or partially biodegradable or biofragmentable.

Further, as stated, the devices and methods disclosed herein can be used to treat a variety of pathologies in a variety of lumens or organs comprising a cavity or a wall. Examples of such lumens or organs include, but are not limited to urethra, bowel, stomach, esophagus, trachea, bronchii, bronchial passageways, veins (e.g. for treating varicose veins or valvular insufficiency), arteries, lymphatic vessels, ureters, bladder, cardiac atria or ventricles, uterus, fallopian tubes, etc.

Finally, it is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unpatentable or unsuitable for its intended use. Also, for example, where the steps of a method are described or listed in a particular order, the order of such steps may be changed unless to do so would render the method unpatentable or unsuitable for its intended use. All reasonable additions, deletions, modifications and alterations are to be considered equivalents of the described examples and embodiments and are to be included within the scope of the following claims.

Thus, it will be apparent from the foregoing that, while particular forms of the invention have been illustrated and described, various modifications can be made without parting from the spirit and scope of the invention.

We claim:

1. A system for creating a continuous indentation in a prostatic urethra, comprising:
a delivery device sized and configured to be placed within a urethra, the delivery device including at least a first projecting needle and a second projecting needle and a first needle housing receiving the first needle and a second needle housing receiving a second needle, wherein at least one projecting needle is configured to project transverse to a longitudinal axis of a distal end portion of the first or second needle housing;
a first distal anchor component and a second distal anchor component each initially housed within and deployable to an outside surface of a prostate by the delivery device while the delivery device remains within the urethra; and
at least one proximal anchor component attached to each of the first and second distal anchors.

2. The system of claim 1, wherein the delivery device is configured to project the needles to equal lengths.

3. The system of claim 1, wherein the delivery device projects the needles to different lengths.

4. The system of claim 1, wherein the first and second housings are arranged in a parallel manner.

5. The system of claim 1, wherein the first and second housings are arranged in a divergent manner.

6. The system of claim 1, wherein the first and second housings are arranged in a crossing manner.

7. The system of claim 1, further comprising an introducer sheath and a drainage assembly attached to the introducer sheath.

8. The system of claim 1, wherein the delivery device includes a snare wire configured to capture and attach connectors extending from the first and second distal anchors.

9. The system of claim 1, further comprising a first proximal anchor and a second proximal anchor.

10. The system of claim 9, wherein the first proximal anchor is attached to the first distal anchor by a first connector segment and the second proximal anchor is attached to the second distal anchor by a second connector segment.

11. The system of claim 1, further comprising a single proximal anchor connected to each of the first and second distal anchors by a connector.

12. The system of claim 1, wherein each of the proximal and distal anchors define split members.

13. The system of claim 1, further comprising an anchor assembly defined by a repeating anchor component along its length.

14. The system of claim 1, wherein the anchor assembly includes a locking structure permitting the anchor assembly to define a closed configuration.

15. The system of claim 1, wherein the proximal anchor includes a bar with two spaced holes, each spaced hole configured to receive a connector extending from one of the first and second distal anchor components.

16. The system of claim 1, further comprising an anchor assembly defined by a curved wire having a length and curvature sized and shaped to span a lobe of a prostate lobe.

17. The system of claim 1, further comprising an anchor assembly including a circular loop formed from flexible material.

18. The system of claim 1, further comprising an anchor assembly including a hoop which expands in width as it contracts.

19. The system of claim 1, further comprising an anchor assembly including an extendable coil.

20. The system of claim 1, further comprising an anchor assembly including an umbrella-like frame.

21. The system of claim 1, further comprising an anchor assembly including prongs adapted to extend longitudinally in a compressed state and perpendicular to a longitudinal direction in a relaxed state.

22. The system of claim 1, further comprising an anchor assembly including a corkscrew body.

23. The system of claim 1, wherein the first distal anchor component or the second distal anchor component are housed within at least one projecting needle.

* * * * *